(12) United States Patent
Charalambides et al.

(10) Patent No.: US 12,336,791 B2
(45) Date of Patent: Jun. 24, 2025

(54) CHEST-WORN DEVICE AND RELATED SYSTEM FOR COMPACT AND PORTABLE PHYSIOLOGICAL MONITORING

(71) Applicant: Lifeware Labs, LLC, Pittsburgh, PA (US)

(72) Inventors: Alexandros Charalambides, Pittsburgh, PA (US); Emily Lickert, Canonsburg, PA (US); Rohith Krishnan Pillai, Pittsburgh, PA (US)

(73) Assignee: LIFEWARE LABS, LLC, Pittsburgh, PA (US)

( * ) Notice: Subject to any disclaimer, the term of this patent is extended or adjusted under 35 U.S.C. 154(b) by 0 days.

(21) Appl. No.: 18/791,844

(22) Filed: Aug. 1, 2024

(65) Prior Publication Data
US 2024/0389866 A1   Nov. 28, 2024

Related U.S. Application Data

(63) Continuation of application No. 18/417,851, filed on Jan. 19, 2024.
(Continued)

(51) Int. Cl.
*A61B 5/0205*  (2006.01)
*A61B 5/00*  (2006.01)
(Continued)

(52) U.S. Cl.
CPC ........ *A61B 5/02055* (2013.01); *A61B 5/0006* (2013.01); *A61B 5/002* (2013.01);
(Continued)

(58) Field of Classification Search
CPC ... A61B 5/02055; A61B 5/0006; A61B 5/002; A61B 5/6833; A61B 5/7267; A61B 5/0002; A61B 5/02; A61B 5/0205; A61B 5/024; A61B 5/02416; A61B 5/02438; A61B 5/103; A61B 5/11; A61B 5/1102; A61B 5/316; A61B 5/318; A61B 5/332; A61B 5/352; A61B 5/68; A61B 5/6801; A61B 5/683; A61B 5/6832; A61B 5/72; G16H 40/67
See application file for complete search history.

(56) References Cited

U.S. PATENT DOCUMENTS

| | | | |
|---|---|---|---|
| 11,241,530 B1 * | 2/2022 | Fridez | A61M 5/1723 |
| 2015/0282713 A1 * | 10/2015 | Fei | A61B 5/0059 600/476 |

(Continued)

*Primary Examiner* — Jennifer Robertson
*Assistant Examiner* — Jonathan Drew Moroneso
(74) *Attorney, Agent, or Firm* — K&L Gates LLP

(57) ABSTRACT

A body-worn patch to be worn by a patient, wherein the body-worn patch comprises a plurality of sensors and a controller. The plurality of sensors comprises a biopotential sensor capable of measuring an electrocardiogram (ECG) signal, an inertial measurement unit capable of measuring a seismocardiogram (SCG) signal, and an optical sensor capable of measuring a photoplethysmography (PPG) signal. The controller is in signal communication with the plurality of sensors and the controller is capable of receiving the ECG signal, the SCG signal, and the PPG signal. The controller is capable of determining a physiological property of the patient based on the ECG signal, the SCG signal, and the PPG signal.

24 Claims, 19 Drawing Sheets

Related U.S. Application Data

(60) Provisional application No. 63/440,061, filed on Jan. 19, 2023.

(51) Int. Cl.
*A61B 5/02* (2006.01)
*A61B 5/316* (2021.01)
*A61B 5/318* (2021.01)
*A61B 5/332* (2021.01)
*G16H 40/67* (2018.01)
*A61B 5/024* (2006.01)
*A61B 5/103* (2006.01)
*A61B 5/11* (2006.01)
*A61B 5/352* (2021.01)

(52) U.S. Cl.
CPC .......... *A61B 5/6833* (2013.01); *A61B 5/7267* (2013.01); *G16H 40/67* (2018.01); *A61B 5/0002* (2013.01); *A61B 5/02* (2013.01); *A61B 5/0205* (2013.01); *A61B 5/024* (2013.01); *A61B 5/02416* (2013.01); *A61B 5/02438* (2013.01); *A61B 5/103* (2013.01); *A61B 5/11* (2013.01); *A61B 5/1102* (2013.01); *A61B 5/316* (2021.01); *A61B 5/318* (2021.01); *A61B 5/332* (2021.01); *A61B 5/352* (2021.01); *A61B 5/68* (2013.01); *A61B 5/6801* (2013.01); *A61B 5/683* (2013.01); *A61B 5/6832* (2013.01); *A61B 5/72* (2013.01)

(56) References Cited

U.S. PATENT DOCUMENTS

| | | | |
|---|---|---|---|
| 2021/0275044 A1* | 9/2021 | Lin | A61B 5/0261 |
| 2023/0058011 A1* | 2/2023 | Du | G16H 40/63 |
| 2024/0090807 A1* | 3/2024 | Rus | A61B 5/7282 |

* cited by examiner

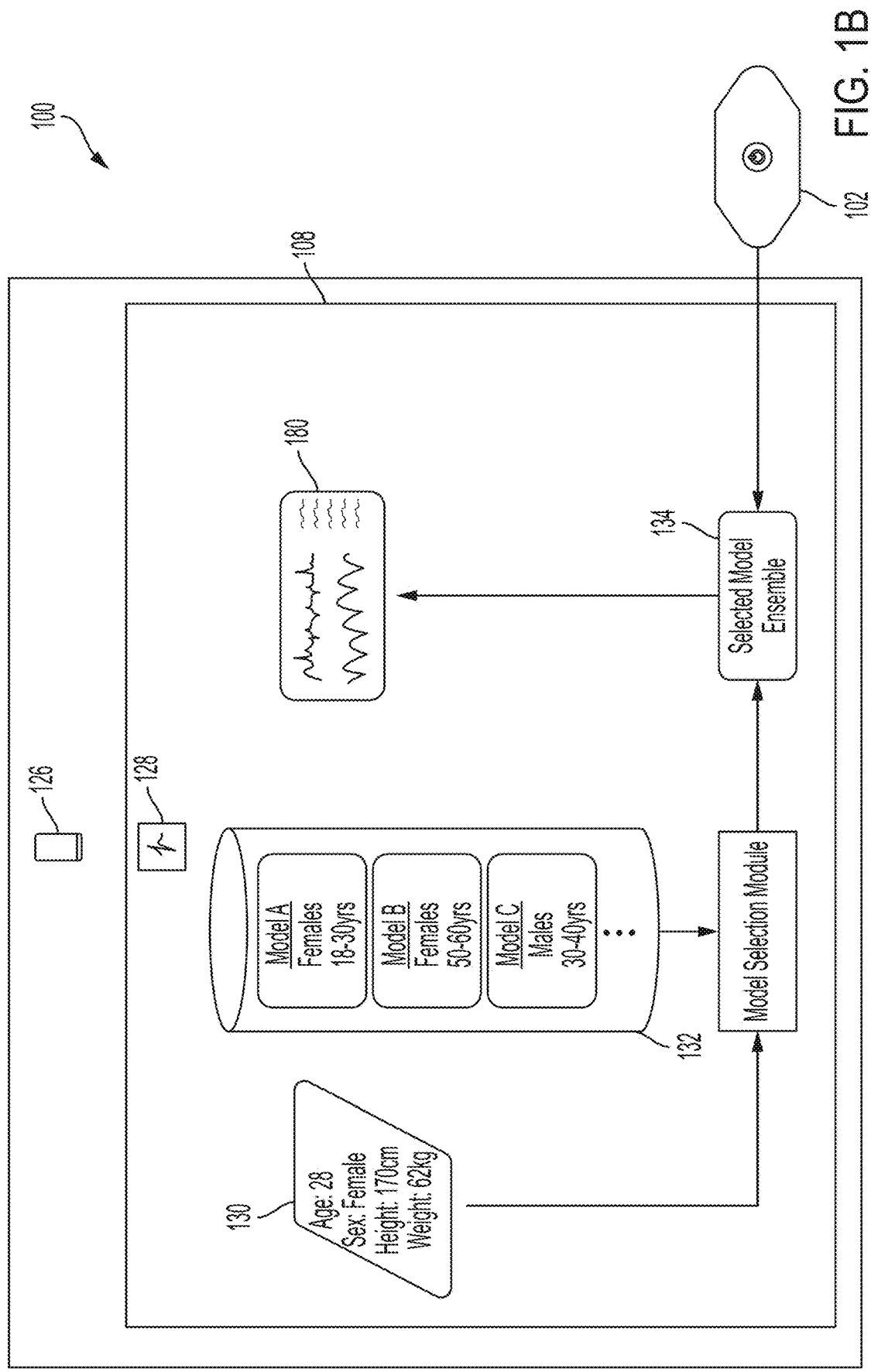

CHEST-WORN DEVICE AND RELATED SYSTEM FOR COMPACT AND PORTABLE PHYSIOLOGICAL MONITORING

PRIORITY CLAIM

The present application is a continuation application of U.S. patent application Ser. No. 18/417,851, filed Jan. 19, 2024, which claims priority to U.S. provisional application Ser. No. 63/440,061, filed Jan. 19, 2023, which is incorporated herein by reference in its entirety.

RELATED U.S. APPLICATION DATA

The present application is related to the following U.S. applications, which are incorporated herein be referenced in their entireties:
Provisional patent application Ser. No. 63/312,284 filed on Feb. 21, 2022 entitled "A Wearable Apparatus and Dashboard for Health Monitoring of Groups of Individuals;"
Nonprovisional application Ser. No. 17/474,906 filed on Sep. 14, 2021 entitled "Wearable Apparatus for Measurement of ElectroCardiogram, Photoplethysmography, Pulse Arrival Time, and Blood Pressure;"
Provisional patent application Ser. No. 63/078,099 file d on Sep. 14, 2020 entitled "Wearable Apparatus for Measurement of ElectroCardiogram, Photoplethysmography, Pulse Arrival Time, and Blood Pressure;"
Provisional patent application Ser. No. 63/025,248 filed on May 15, 2020 entitled "Wearable Apparatus and Data Pipeline for Telemedicine Disease Monitoring;" and
Nonprovisional application Ser. No. 16/698,574 filed on Nov. 27, 2019, entitled "Wearable Device with Mechanical Spring to Detect Pulse Transit Time."

BACKGROUND

In emergency medicine, it is important for first responders to collect the vital signs of the sick and injured to triage and administer effective care. Current state-of-the-art instruments are typically large, heavy apparatuses that involve the use of cables that interface with the patient. Although these devices are accurate and measure a wide array of vital signs, they are cumbersome, expensive, and only moderately portable. Therefore, these are typically utilized only in and around transport vehicles, such as ambulances and helicopters. In the case of austere environments, where size and weight are of the utmost importance, these apparatuses are not viable. It is therefore desirable to miniaturize this style of equipment without compromising on its physiological monitoring capabilities

SUMMARY

In one general aspect, the present disclosure is directed to a body-worn patch to be worn by a patient, wherein the body-worn patch comprises a plurality of sensors and a controller. The plurality of sensors comprises a biopotential sensor capable of measuring an electrocardiogram (ECG) signal, an inertial measurement unit capable of measuring a seismocardiogram (SCG) signal, and an optical sensor capable of measuring a photoplethysmography (PPG) signal. The controller is in signal communication with the plurality of sensors and the controller is capable of receiving the ECG signal, the SCG signal, and the PPG signal. The controller is capable of determining a physiological property of the patient based on the ECG signal, the SCG signal, and the PPG signal.

In another general aspect, the present disclosure is directed to a method for determining a physiological property of a patient with a body-worn patch, the method comprising measuring, by a biopotential sensor of a body-worn patch device, an ECG signal of the patient; measuring, by an inertial measurement unit of the body-worn patch device, an SCG signal of the patient; and measuring, by an optical sensor of the body-worn patch device, a PPG signal of the patient. The method further comprises receiving, by a controller, the ECG signal, the SCG signal, and the PPG signal and determining, by the controller, a physiological property of the patient based on the ECG signal, the SCG signal, and the PPG signal.

The present disclosure can provide both a smaller and more compact instrument for measuring physiological properties without compromising the accuracy of the measurements. The small form-factor of the body-worn patch can allow medical personnel to easily carry multiple measuring devices into environments current measuring devices are unable to reach. Additionally, a mobile computing device, such as a cellphone, can be used to receive the signals from the device and display the resulting physiological properties, thereby further reducing the burden on medical personnel. These and other benefits realizable from various embodiments of the present disclosure will be apparent from the description that follows.

BRIEF DESCRIPTION OF THE DRAWINGS

Various embodiments of the present disclosure are described herein by way of example in connection with the following figures.
FIG. 1B illustrates a system for determining a physiological property using a body-worn patch and a machine learning model in accordance with the present disclosure.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Certain exemplary aspects of the present disclosure will now be described to provide an overall understanding of the principles of the apparatus, function, manufacture, and use of the apparatus and methods disclosed herein. An example or examples of these aspects are illustrated in the accompanying drawing. Those of ordinary skill in the art will understand that the apparatus, articles, and methods specifically described herein and illustrated in the accompanying drawing are non-limiting exemplary aspects and that the scope of the various examples of the present disclosure is defined solely by the claims. The features illustrated or described in connection with one exemplary aspect may be combined with the features of other aspects. Such modifications and variations are intended to be included within the scope of the present disclosure.

In the case of austere environments, where size and weight are of the utmost importance, current devices for measuring vital signals may not be viable as they can be heavy, bulky, expensive, and/or limited in capability. The body-worn patch according to the present disclosure can be viable for austere environments, as the system can be light, small, inexpensive, and fully capable of measuring a variety of vital signals. For example, the present disclosure provides a body-worn patch that can comprise a plurality of sensors and a controller. The plurality of sensors can comprise a biopotential sensor capable of measuring an electrocardiogram (ECG) signal, an inertial measurement unit capable of measuring a seismocardiogram (SCG) signal, and an optical sensor capable of measuring a photoplethysmography (PPG) signal. The controller can be in signal communication with the plurality of sensors. The controller can be capable of receiving the ECG signal, the SCG signal, and the PPG signal. The controller can be capable of determining a physiological property of the patient based on the ECG signal, the SCG signal, and the PPG signal The body-worn patch described herein can simultaneously measure a wide array of vital signals (e.g., ECG signal, SCG signal, PPG signal) while maintaining a highly compact form factor. The system can use these vital signals to determine and monitor a variety of physiological properties of a patient, including blood pressure and/or compensatory reserve measure, among others. The small form factor and highly accurate vital measurement capabilities can be desirable for medical professionals in austere environments, such as combat medics, EMTs, and other first responders.

Figure 1A:
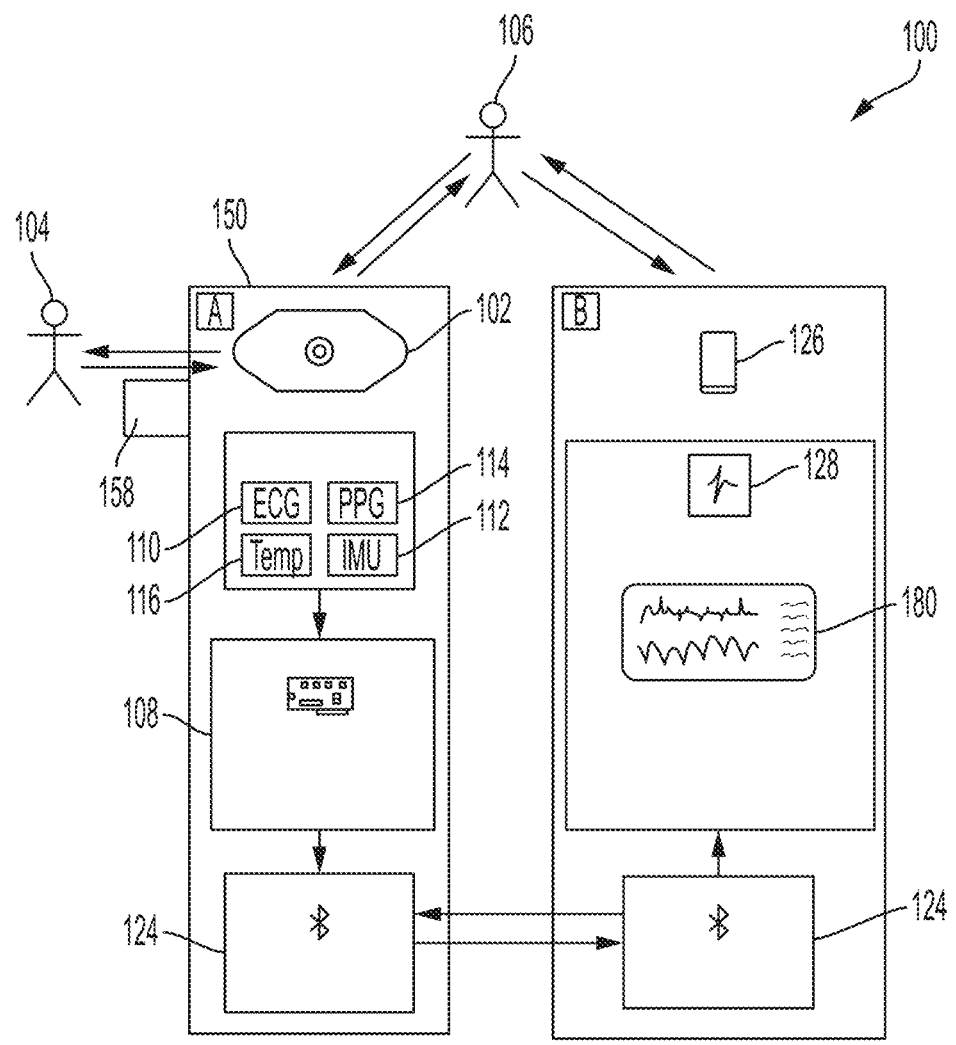
FIG. 1A illustrates a system for determining a physiological property using a body-worn patch in accordance with the present disclosure.

Referring to FIG. 1A, a system 100 comprising a body-worn patch 102 to be worn by a patient 104 is provided. As illustrated, the body-worn patch 102 can comprise a plurality of sensors and a controller 108. The plurality of sensors can comprise a biopotential sensor 110 capable of measuring an electrocardiogram (ECG) signal, an inertial measurement unit (IMU) 112 capable of measuring a seismocardiogram (SCG) signal, an optical sensor 114 capable of measuring a photoplethysmography (PPG) signal, and a temperature sensor 116 capable of measuring the temperature of the patient or the temperature of the environment. The body-worn patch 102 can be capable of measuring the ECG signal, SCG signal, and PPG signal simultaneously.

Figure 3A:
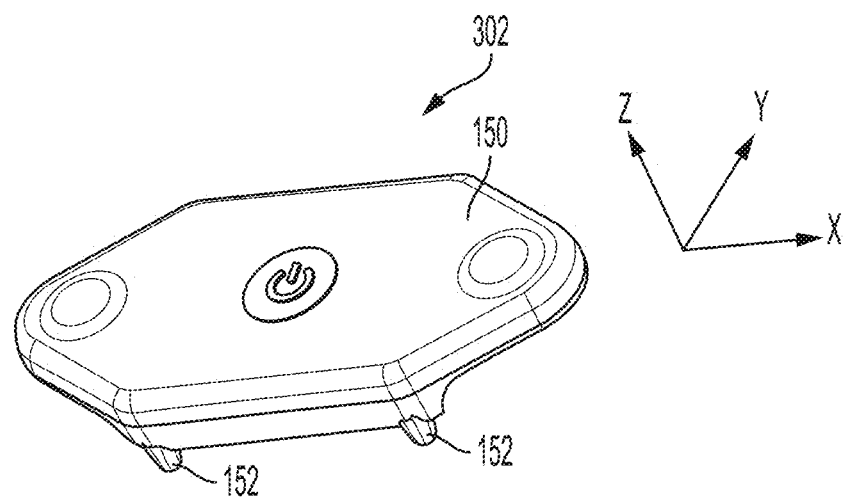
FIG. 3A is a perspective view of the body-worn patch in accordance with the present disclosure.
Figure 3B:
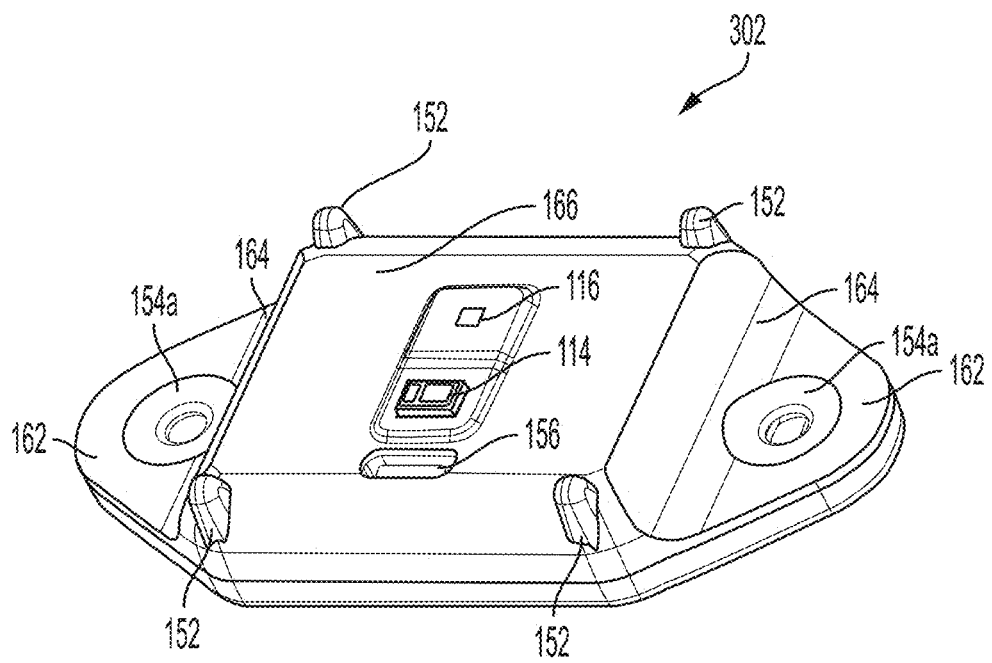
FIG. 3B is a perspective view of the bottom of the body-worn patch in accordance with the present disclosure.

The biopotential sensor 110 and IMU 112 may be at least partially enclosed within a housing 150 of the body-worn patch 102. The housing 150 may be made from various materials, such as, for example, a polymer (e.g., a tough plastic, such as polycarbonate/acrylonitrile butadiene styrene (PC/ABS)) in order to protect the electronics therein while pressing skin-side sensors (e.g., optical sensor 114 and temperature sensor 116) into the patient's 104 skin. The optical sensor 114 and temperature sensor 116 may not be fully enclosed in the housing 150 and may protrude from the bottom surface 166 of the housing 150 in order to be pressed into the patient's skin 104 during use, which can improve the signal-to-noise ratio, as shown in FIG. 3B, for example.

The biopotential sensor 110 can be capable of measuring an ECG signal. For example, as shown in FIG. 1A, the biopotential sensor 110 can be electrically connected to an electrode portion 158 for conducting and measuring biopotential (e.g., ECG signal) from a patient's body 104. The electrode portion 158 can be capable of contacting skin of the patient 104 via electrodes to enable electrical communication between the patient 104 and the body-worn patch 102. The electrical connection can be removable as the application may require. In various examples, the biopotential sensor 110 can be electrically connected to at least two electrodes. In certain examples, the ECG signal can be sampled at a rate in a range of 50 Hz to 500 Hz, such as, for example, 100 Hz to 300 Hz or 200 Hz.

Figure 2A:
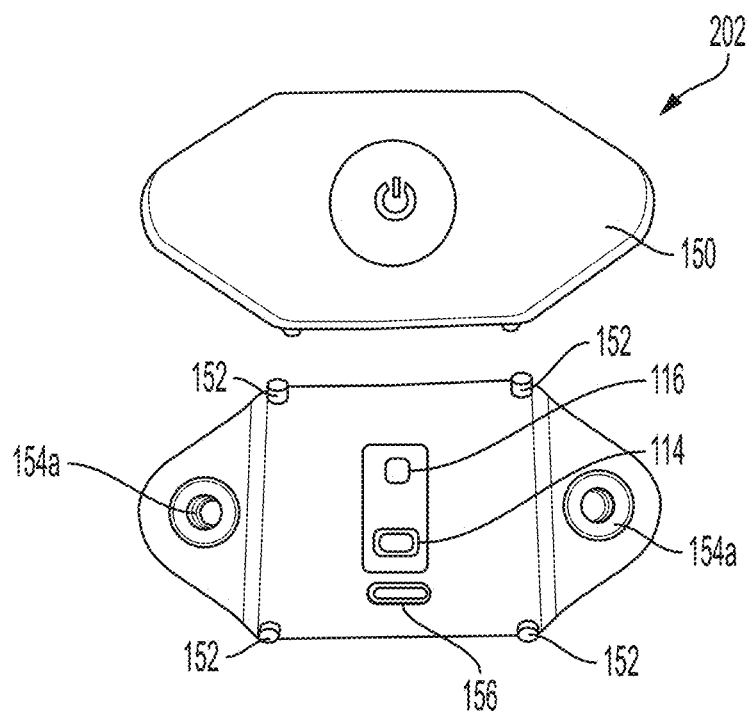
FIG. 2A is a top and bottom view of a body-worn patch in accordance with the present disclosure.
Figure 2B:
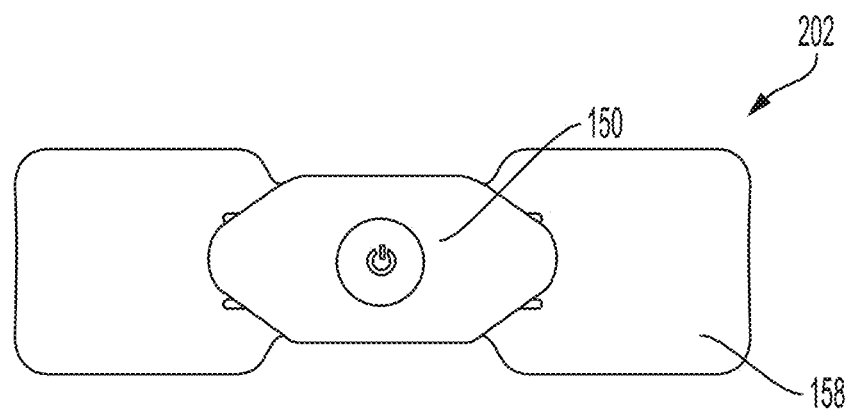
FIG. 2B is a top view of the body-worn patch and electrode portion in accordance with the present disclosure.
Figure 2C:
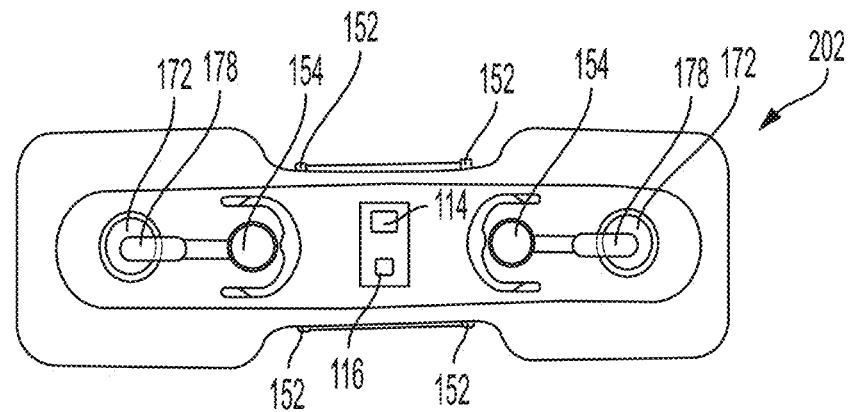
FIG. 2C is a bottom view of the body-worn patch and electrode portion in accordance with the present disclosure.
Figure 2D:
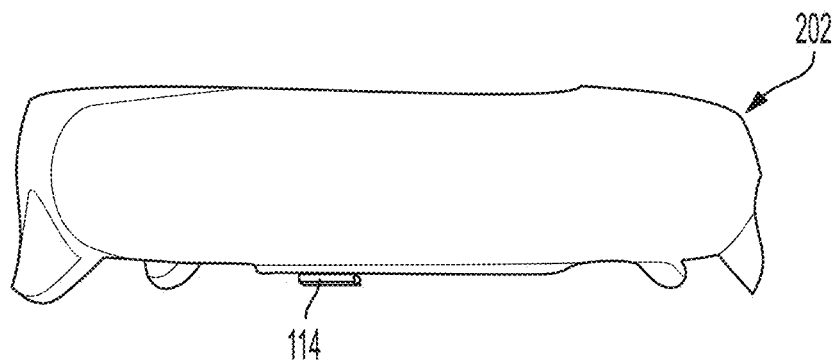
FIG. 2D is a side view of the body-worn patch in accordance with the present disclosure.
Figure 2E:
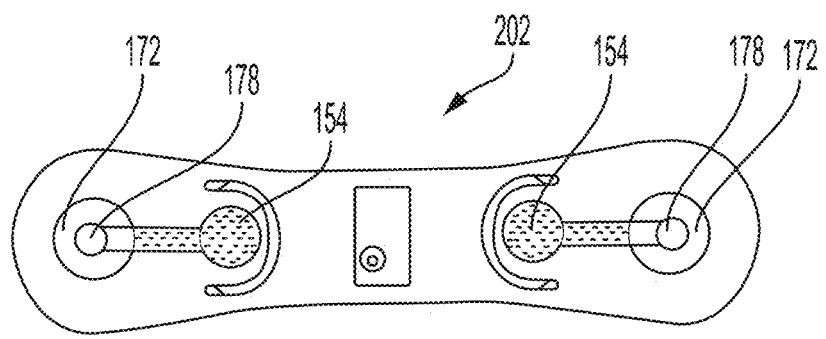
FIG. 2E is a bottom view of the body-worn patch and electrode portion in accordance with the present disclosure, wherein a release liner is attached.

As shown in FIGS. 2C and 2E, the electrode portion 158 can comprise electrodes 178, which can be removably adhered to skin using a skin-side adhesive 172. The electrodes 178 are electrically connected to the male portion of the electrode snaps 154 disposed on the electrode portion 158. When the male and female portions of the electrode snaps 154 are connected, an electrical connection between the electrode portion 158 and the body-worn patch 202 can be created. The electrodes 178 may be spaced a distance apart on the patient 104 and the housing 150 of the body-worn patch 202 can extend from the distance intermediate the electrodes 170 and/or be located therebetween.

Figure 4A:
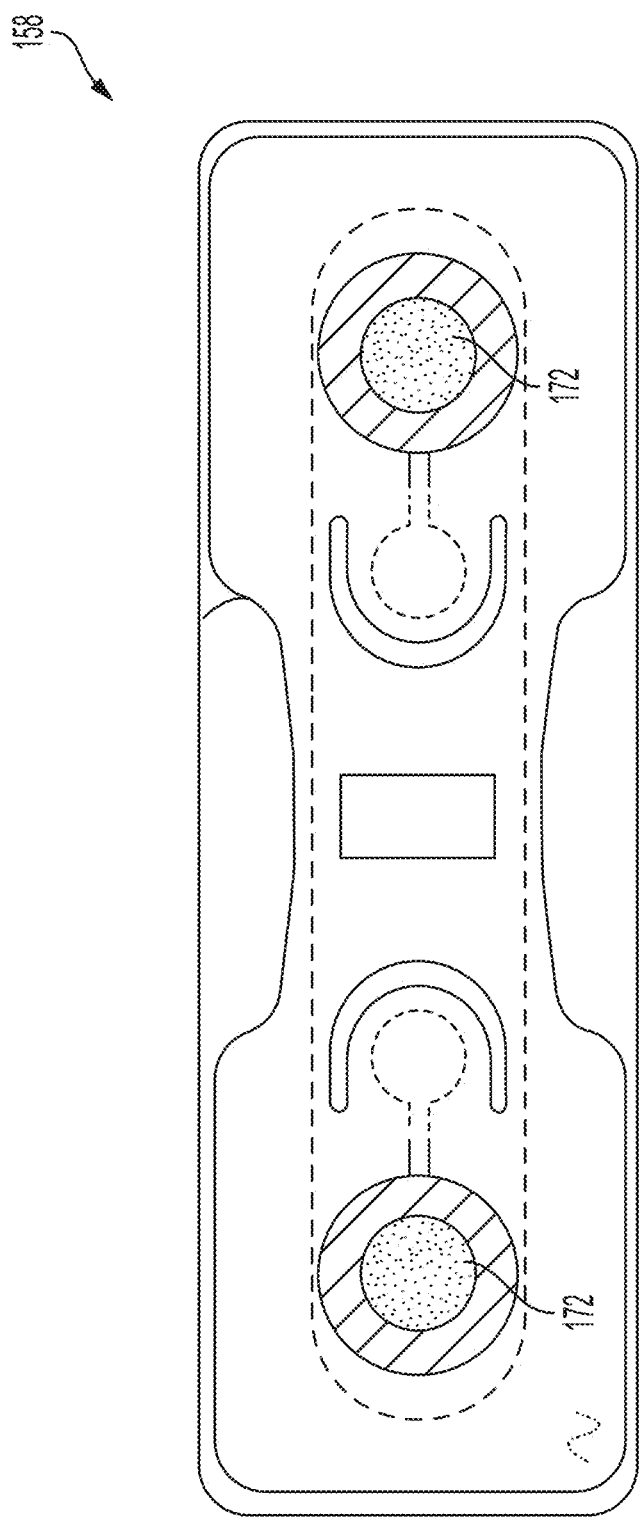
FIG. 4A is a schematic diagram of the electrode portion for use with a body-worn patch in accordance with the present disclosure.
Figure 4B:
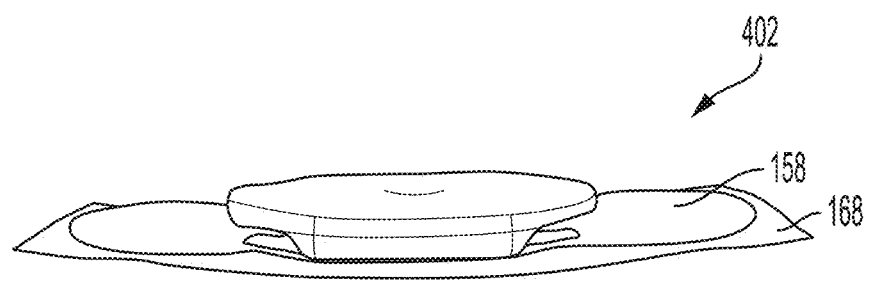
FIG. 4B is a body-worn patch and electrode portion with a release liner in accordance with the present disclosure.
Figure 4C:
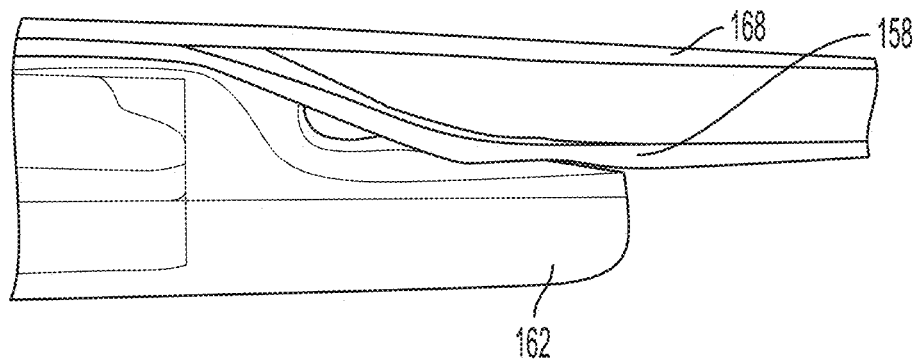
FIG. 4C is an enhanced view of the body-worn patch and electrode portion with a release liner shown in FIG. 4B.
Figure 4D:
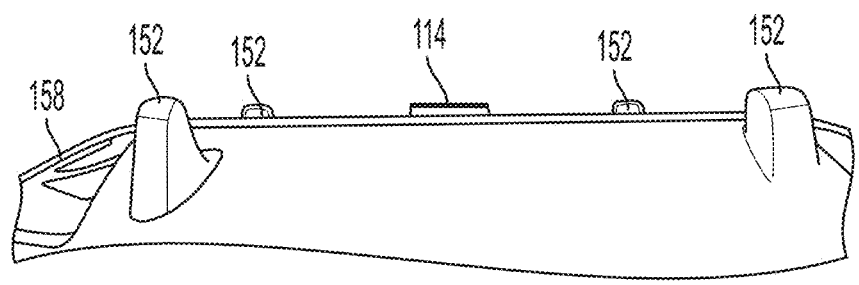
FIG. 4D is a side view of the body-worn patch and electrode portion with release liner in accordance with the present disclosure.
Figure 4E:
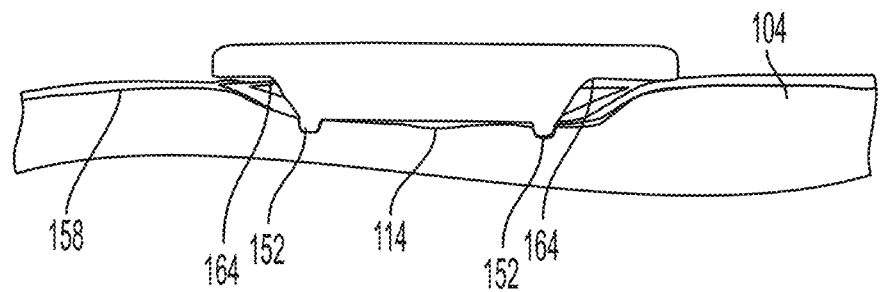
FIG. 4E is a side view of the body-worn patch and electrode portion attached to a patient in accordance with the present disclosure.
Figure 4F:
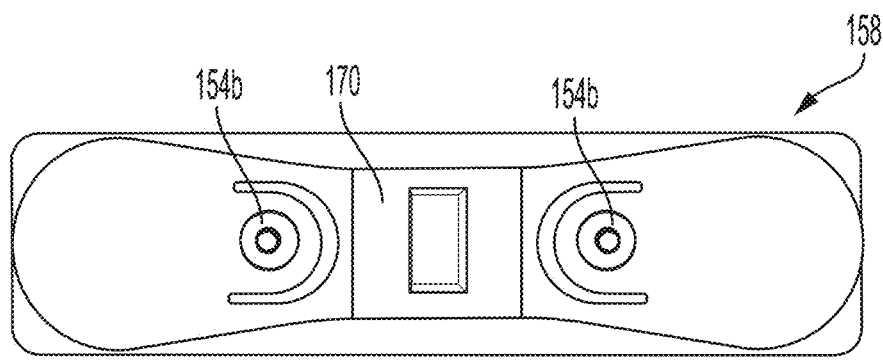
FIG. 4F is a top view of the electrode portion for use with a body-worn patch in accordance with the present disclosure.

Referring again to FIG. 1A, the electrode portion 158 can be removably connected to the housing 150 of the body-worn patch 102 via a fastener, such as, for example, a device-side adhesive (e.g., adhesive 170 as illustrated in FIG. 4F), mechanical snaps (e.g., snaps 154 as illustrated in FIG. 4F), metallic buttons, or a combination thereof. For example, referring to FIGS. 2A, 2C, and 4F, the electrode portion 158 may be coupled to the body-worn patch 202 via electrode snaps 154, wherein the male side of each electrode snap 154b can include a metallic post, for example, that snaps into an opening of the female portion of the electrode snap 154a located on the housing 150 of the body-worn patch 202. As such, the electrode snaps 154 can be located further away from the patient's skin 104 than the bottom surface 166 of the housing 150 of the body-worn patch 302, as shown in FIGS. 3B and 4E.

Figure 4G:
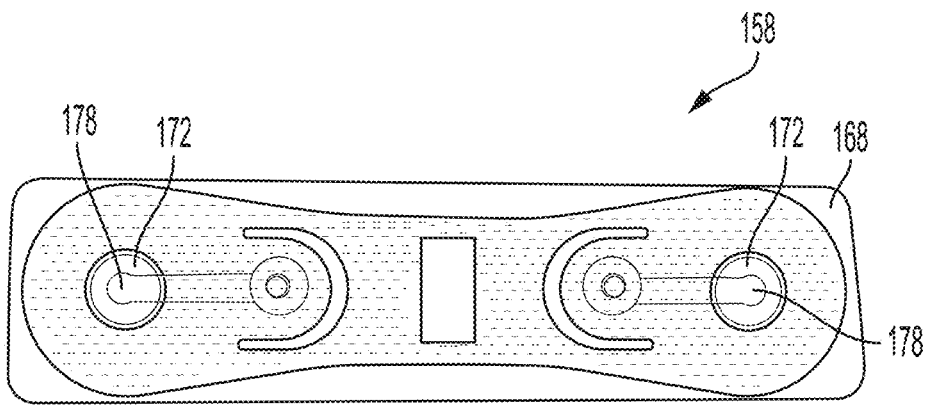
FIG. 4G is a bottom view of the electrode portion with the release liner attached for use with a body-worn patch in accordance with the present disclosure.
Figure 4H:
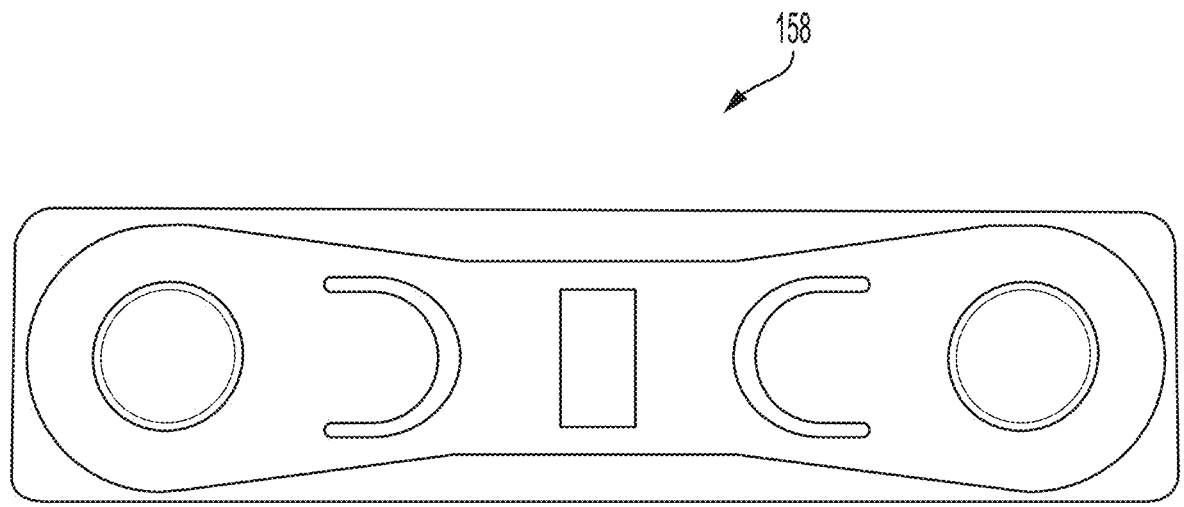
FIG. 4H is the release liner corresponding to an electrode portion for use with a body-worn patch in accordance with the present disclosure.
Figure 5A:
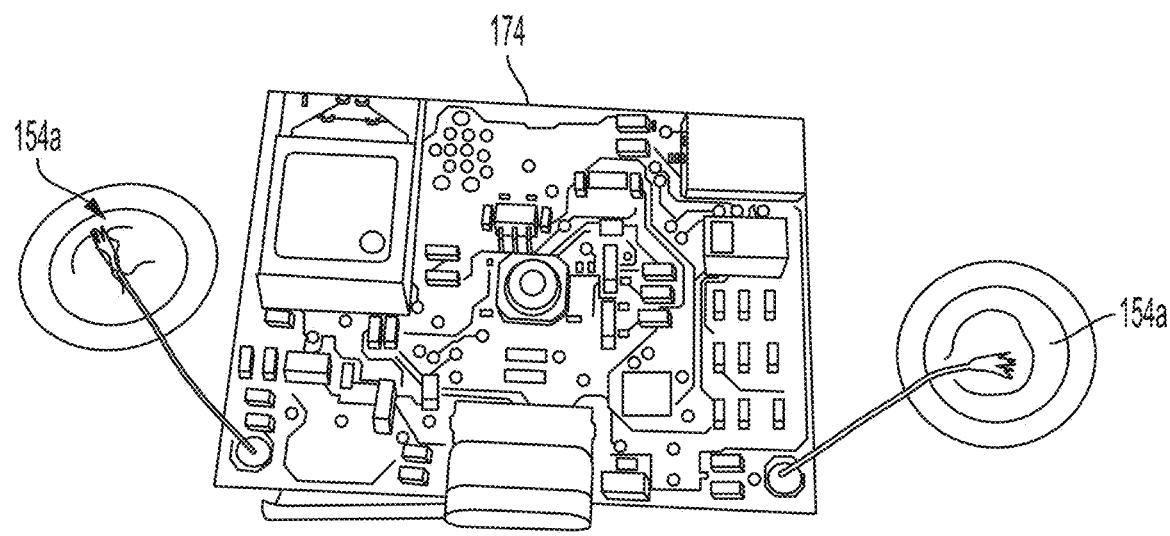
FIG. 5A is a circuit board and electrode snaps for use in a body-worn patch in accordance with the present disclosure.
Figure 5B:
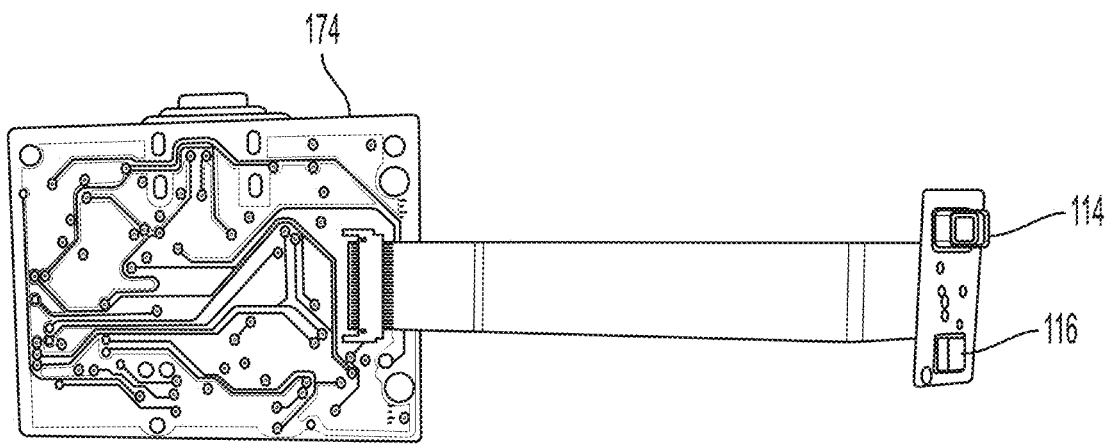
FIG. 5B is the primary circuit board electrically coupled to a secondary circuit board for use in a body-worn patch in accordance with the present disclosure.
Figure 5C:
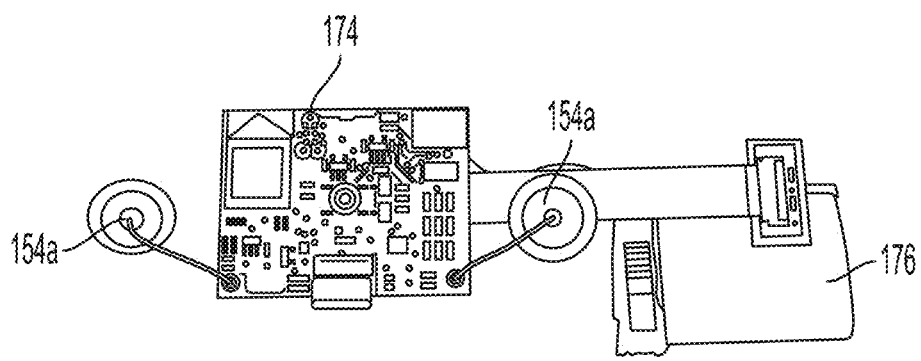
FIG. 5C is a top view of the circuit boards shown in FIGS. 5A and 5B attached to a battery in accordance with the present disclosure.
Figure 5D:
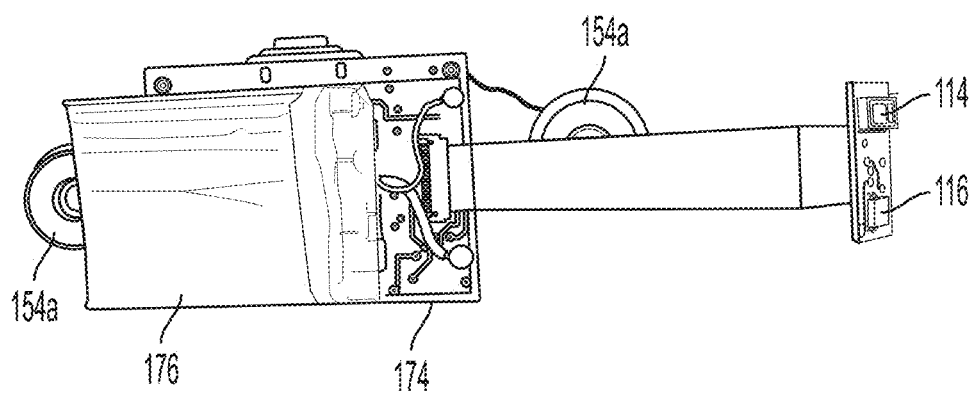
FIG. 5D is a bottom view of the circuit boards shown in FIGS. 5A and 5B attached to a battery in accordance with the present disclosure.

Referring to FIG. 4G, the electrode portion 158 may be attached to the patient 104 via a skin-side adhesive 172. In various examples the skin-side adhesive 172 may be an adhesive hydrogel that can be attach to the patient 104 despite dirt, sweat, and/or blood thereon. The skin-side adhesive 172 can adhere to the patient's body 104 in a manner sufficient to pick up the biopotentials from the patient 104.

Figure 3C:
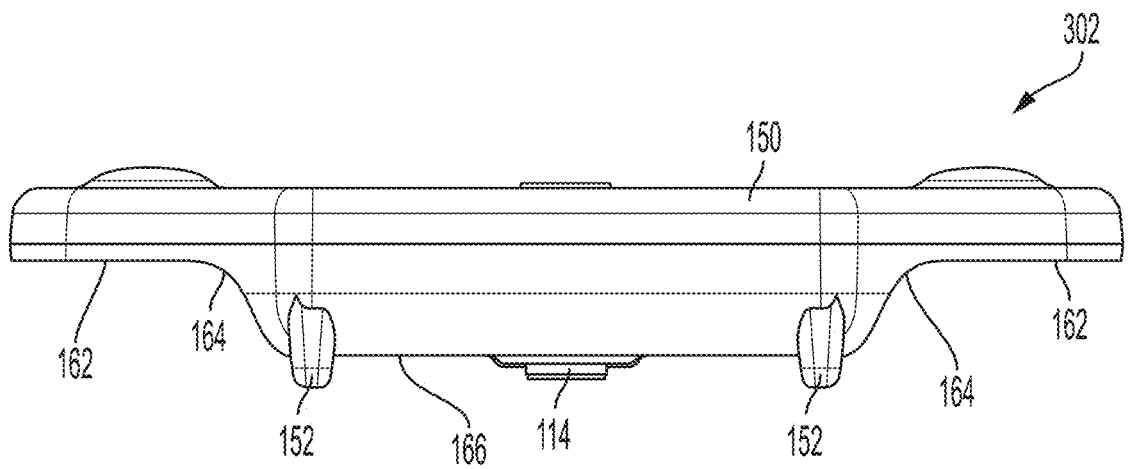
FIG. 3C is a front view of the body-worn patch in accordance with the present disclosure.
Figure 3D:
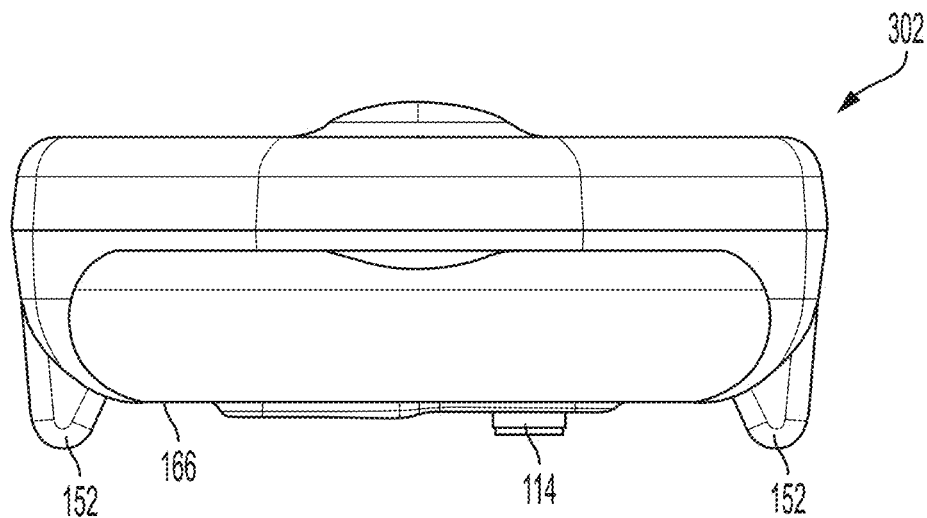
FIG. 3D is a side view of the body-worn patch in accordance with the present disclosure.
Figure 3E:
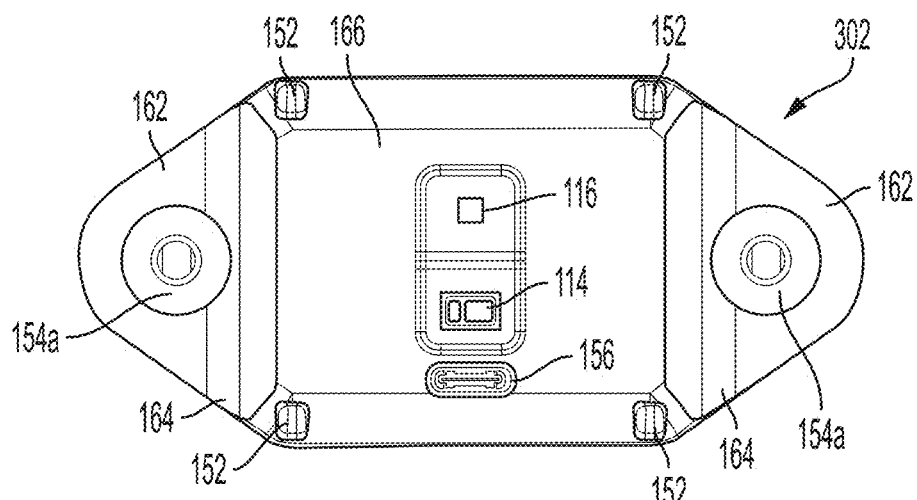
FIG. 3E is a bottom view of the body-worn patch in accordance with the present disclosure.
Figure 3F:
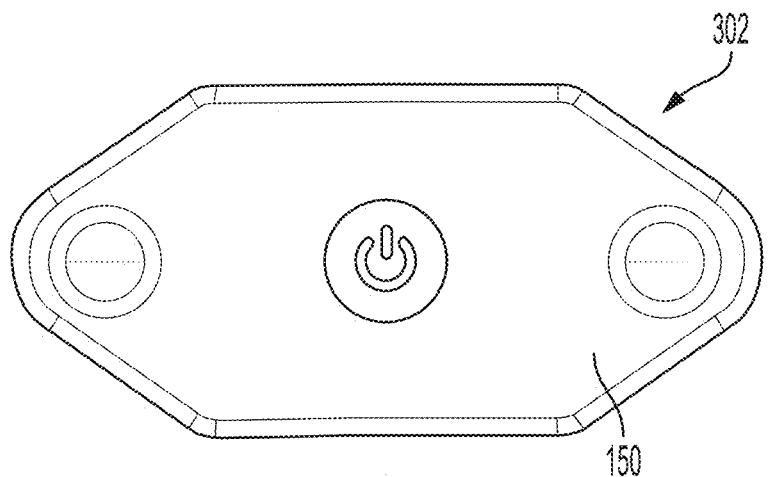
FIG. 3F is a top view of the body-worn patch in accordance with the present disclosure.
Figure 3G:
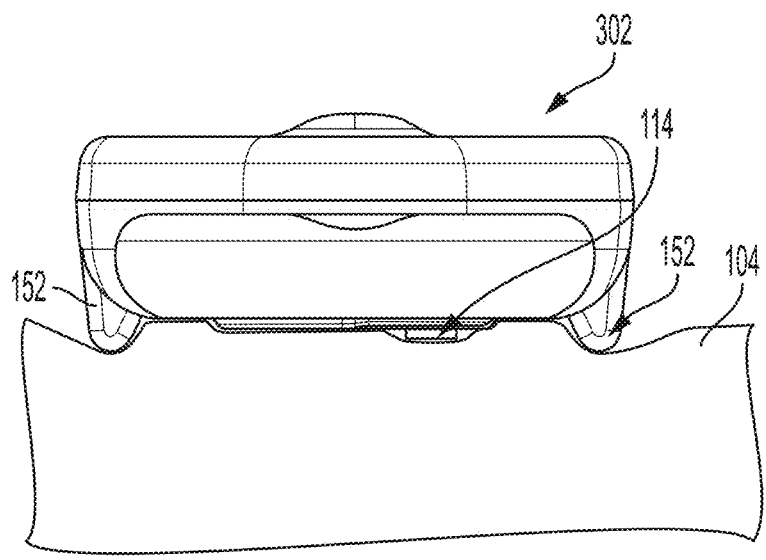
FIG. 3G is a side view of the body-worn patch placed against a patient's skin in accordance with the present disclosure.
Figure 3H:
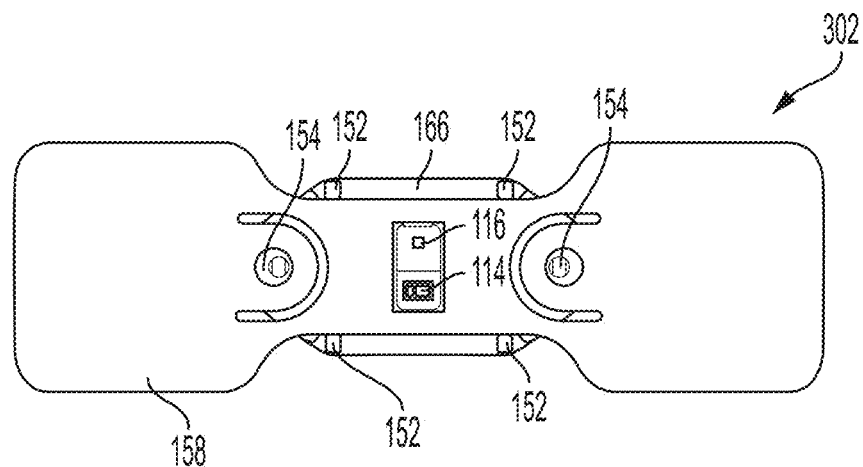
FIG. 3H is a bottom view of the body-worn patch and electrode portion in accordance with the present disclosure.

Referring to FIG. 3C, the housing 150 of the body-worn patch 302 may comprise curved corners 164 such that the electrode snaps 154 are positioned further away from the patient's skin 104 and the bottom surface 166 of the housing 150 of the body-worn patch 302. As shown in FIG. 4E, the electrode portion 158 can lay planar with the patient's skin 104, such that the male portion of the electrode snaps 154b located on the electrode portion 158 raise off the patient's skin 104 to meet the female portion of the electrode snaps 154a on the housing 150 of the body-worn patch 402. The electrode portion 158 may be highly tacky, such that it pulls the entire device down into the skin with this connection.

Referring again to FIG. 1A, the IMU 112 can be capable of measuring an SCG signal 120. The IMU 112 may include a device capable of measuring specific gravity, forces, rates, and/or orientation. The IMU 112 may include at least one of an accelerometer, a gyroscope, and a magnetometer. In various examples, the accelerometer may be configured for single axis measurements to measure vibration. For example, in certain examples, the SCG signal is acquired from the acceleration in the z-axis using the IMU 112, which aligns closely with the dorsoventral axis. As such, SCG can be a measure of the dorsoventral accelerations. In various examples, the IMU 112 can be sampled at a rate in a range of 5 Hz to 500 Hz, such as, for example, 50 Hz to 200 Hz or 100 Hz.

The optical sensor 114 can be capable of measuring light rays in order to measure a PPG signal of the patient 104. The optical sensor 114 may comprise a light source and a light detector, such that the optical sensor 114 may be capable of sensing both visible light and infrared light. The optical sensor 114 may be, in certain examples, a pulse ox sensor. In various examples, the PPG signal can be sampled at a rate in a range of 5 Hz to 500 Hz, such as, for example, 50 Hz to 200 Hz or 100 Hz.

Referring to FIG. 3C, in various examples, the optical sensor 114 may be integrated with the body-worn patch 302 such that the optical sensor 114 protrudes from the housing 150 in order to contact the skin of the patient 104. For example, the optical sensor 114 may protrude from the bottom surface 166 of the housing 150 in a range of 0.05 mm to 5 mm, such as for example, 0.5 mm to 2.5 mm or 1.5 mm. Pressing the optical sensor 114 into the patient's skin 104 increases the pressure, thereby improving the signal-to-noise ratio of the PPG signal. The closer the lights and measurement units on the optical sensor 114 are to the skin 104 with no air space between, the better the acquired PPG signal will be, thereby improving the calculated physiological property of the patient 104.

Referring to FIG. 3B, to mitigate potential breakage of the optical sensor 114, the housing 150 may include protrusions 152 around the perimeter of the bottom surface 166 of the housing 150 to protect the optical sensor 114. These protrusions 152, or "feet," may be integrated into the housing 150 of the body-worn patch 302. The protrusions 152 extend further from the bottom surface 166 of the housing 150 than the optical sensor 114 to protect the optical sensor 114, while still allowing the optical sensor 114 to contact the skin 104. Thus, when the body-worn patch 302 with protrusions 152 is placed on the skin of a patient 104, the skin 104 can deform around the protrusions 152 to be pressed into the optical sensor 114 prior to generating measurements.

Referring again to FIG. 1A, the plurality of sensors of the system may further comprise a temperature sensor 116. Like the optical sensor 114, in various examples the temperature sensor 116 may be integrated with the body-worn patch 102 such that it also protrudes from the bottom surface 166 of the housing 150 in order to contact a skin of the patient 104, as shown in FIG. 3B. Also like the optical sensor 114, the temperature sensor 116 can be protected by protrusions 152 located on the bottom surface 166 of the housing 150 of the body-worn patch 302.

Referring to FIGS. 4E-4G, and as discussed herein, the electrode portion 158 of the biopotential sensor 110 may interface with the bottom surface 166 of the housing 150 via a device-side adhesive 170 and with the skin of the patient 104 via a skin-side adhesive 172, which may aid in pulling the patient's skin 104 around the protrusions 152 and into the optical sensor 114 and temperature sensor 116. Thus, the protrusions 152 can protect the skin-side sensors (e.g., optical sensor 114 and temperature sensor 116) without disturbing the interface between the patient's skin 104 and the measurement sensors. The protrusions 152 can be rounded to avoid damaging the surrounding tissue and harming the patient.

Referring again to FIG. 1A, the body-worn patch 102 further comprises a controller 108, which is in signal communication with the plurality of sensors, such that the controller 108 is capable of receiving the ECG signal, the SCG signal, and the PPG signal. As used herein, the term "controller" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or FPGA), state machine circuitry, firmware that stores instructions executed by programmable circuitry, and any combination thereof. The controller 108 may, be embodied, collectively or individually, as circuitry that forms part of a larger system, for example, an IC, an ASIC, a SoC, a desktop computer, a laptop computer, a tablet computer, a server, a smart phone, etc. Accordingly, as used herein, a "controller" can comprise electrical circuitry having at least one discrete electrical circuit, electrical circuitry having at least one IC, electrical circuitry having at least one application-specific IC, electrical circuitry forming a general-purpose computing device configured by a computer program (e.g., a general-purpose computer configured by a computer program that at least partially carries out processes and/or devices described herein or a microprocessor configured by a computer program that at least partially carries out processes and/or devices described herein), electrical circuitry forming a memory device (e.g., forms of RAM), and/or electrical circuitry forming a communications device (e.g., a modem, communications switch, or optical-electrical equipment). The subject matter described herein may be implemented in an analog or digital fashion, or some combination thereof.

The controller 108 may be connected to a remote server, such as a cloud computing system. In various examples, the controller 108 may be located remotely or, alternatively, the controller may be physically integrated in the body-worn patch 102. The controller 108 may include a mobile application 128 for use on a mobile computing device 126, such as a smartphone or a tablet computer, for example.

The body-worn patch 102 may further comprises a wireless communication circuit 124 capable of wirelessly transmitting the ECG signal, the SCG signal, and the PPG signal to the controller 108, a secondary controller, or a combination thereof. The wireless communication circuit 124 may transmit signals using Bluetooth, over the internet, or via other wireless communication protocols to various receivers. In various examples, the system may be capable of wirelessly transmitting data from the body-worn patch 102 to remote medical personnel via the wireless communication circuit 124. In certain examples, the remote medical personnel can be artificial intelligence software that is trained to triage and identify possible pathologies, which can then instruct the onsite medical personnel with specific care.

Figure 1C:
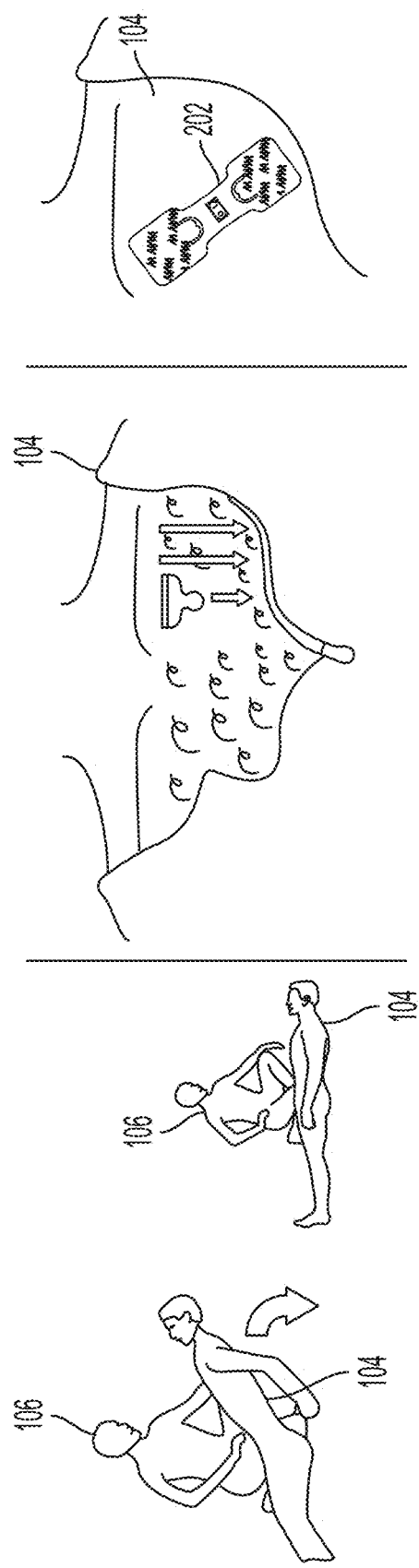
FIG. 1C illustrates applying a body-worn patch to a patient in accordance with the present disclosure.
Figure 1D:
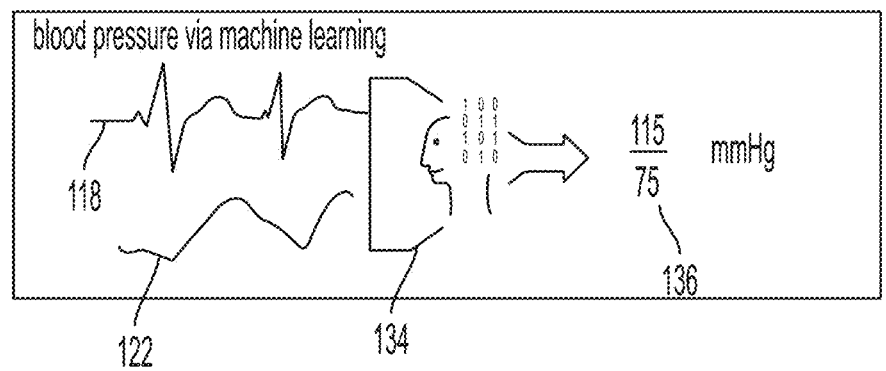
FIG. 1D illustrates a process for determining a physiological property using inputs from a body-worn patch and a machine learning model in accordance with the present disclosure.
Figure 6A:
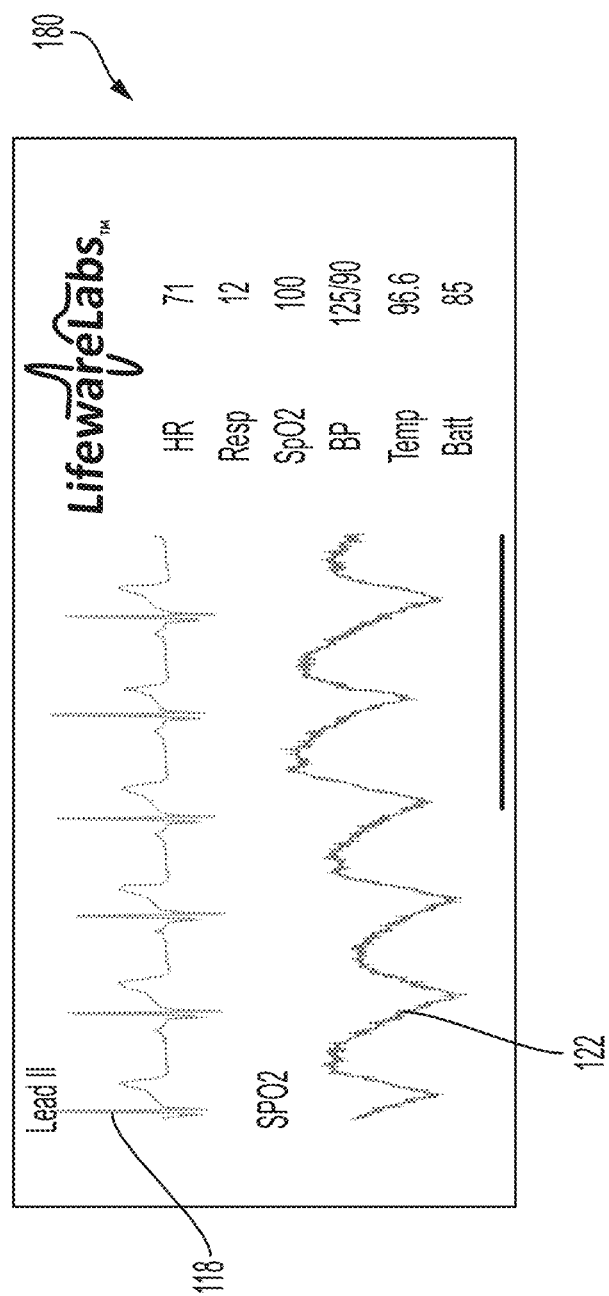
FIG. 6A is a display output for physiological properties of a patient measured using a body-worn patch in accordance with the present disclosure.

Referring to FIGS. 1A, the controller 108 of the system 100 can be capable of determining and displaying 180 a physiological property of the patient 104 based on an ECG signal, an SCG signal, and a PPG signal. The physiological property may be a vital sign of the patient. In various examples, as shown in FIG. 6A, the physiological property may include heart rate, respiration rate, oxygen saturation, temperature, blood pressure, compensatory reserve measure, stroke volume, total peripheral resistance, cardiac output, and/or ejection fracture. As shown in FIG. 1F, the controller 108 can be further capable of aligning the ECG signal 118, the SCG signal 120, and the PPG signal 122 based on time. As shown in FIG. 1F, various features, vital signs, and intermediate metrics may be derived from the ECG signal 118, SCG signal 120, and PPG signal 122, alone or in combination with each other. These features can relate to underlying physiological characteristics, such as the mechanical motion of the heart, the speed of the cardiovascular pulse pressure wave, or the shape of the cardiovascular pulse pressure wave.

Referring to FIG. 1F, in various examples an R-wave 138 can be determined from the ECG signal 118. The R-wave 138 is the first positive wave or first upward deflection of the QRS complex. From the SCG signal 120, an AO peak 140, or AO wave, can be determined. The AO peak 140 is the maximum peak of the SCG signal 120 and it corresponds to the aortic valve opening. When analyzed in view of the R-wave 138 from the ECG signal 118, the AO peak 140 of the SCG signal 120 may be used to determine a pre-ejection period (PEP) 144. Finally, a PPG onset 142, or foot, may be determined from the PPG signal 122. The PPG onset 142 refers to the beginning of the pulse in the systolic phase, where blood with oxygen flows at the measuring site. When analyzed in view of the AO peak 140 from the SCG signal 120, the PPG onset 142 of the PPG signal 122 may be used to determine a pulse transit time (PTT) 146. Further, when analyzed in view of the R-wave 138 of the ECG signal 118, the PPG onset 142 of the PPG signal 122 may be used to calculate a pulse arrival time (PAT) 148. In other words, by aligning the signals, the controller 108 can identify key features of the ECG signal 118, the SCG signal 120, and the PPG signal 122 as described above in order to calculate various signal characteristics, including PAT 148, PTT 146, and PEP 144. The controller 108 can then use these signal characteristics to determine the physiological properties of the patient, including, but not limited to, blood pressure and/or compensatory reserve measure.

Referring now to FIG. 1B, in various examples, the controller 108 of the system 100 may be further capable of receiving demographic information 130 of the patient 104, wherein the controller 108 determines the physiological property based on the ECG signal 118, the SCG signal 120, the PPG signal 122, and the patient's demographic information 130. The demographic information 130 can comprise at least one of an age of the patient, a gender of the patient, a height of the patient, a weight of the patient, and a body mass index (BMI) of the patient.

As shown in FIG. 1B, in addition to using the plurality of characteristics 144, 146, 148 based on the signals 118, 120, 122 to determine the physiological properties of the patient 104, the controller 108 may further determine the physiological properties of the patient 104 using a machine-learning model 134. The machine-learning model 134 may comprises at least one model selected from the group consisting of linear regression, decision tree, gradient boosted machine, ensemble method, and a deep learning based neural network.

The machine-learning model 134 may be generated in advance of the deployment of the system 100. The machine-learning model 134 may be stored by the controller 108, such that the controller 108 can access the machine-learning model 134 to enhance the calculation of the physiological properties. In order to create the machine-learning model 134, ECG signals, SCG signals, and PPGs signals may be collected and physiological properties may be measured using known methods (e.g., using a blood pressure cuff for blood pressure measurements) simultaneously to create a ground truth comparison. By performing this experiment across a large cross-section of the population, the relationship between the signals (and the corresponding signal characteristics) and the desired physiological properties can be established over a wide range demographic combinations (including, e.g., height, weight, age, and gender combinations) to effectively create a massive calibration table. Multiple people with the same demographic information can be measured and the results can be averaged to create a more accurate calibration table.

The inclusion of patient demographic information 130 may further enhance physiological property determinations, since demographic information 130 helps to account for anatomical differences between patients. FIG. 1B shows, for example, that such demographic information 130 may include height, weight, sex, and age.

In various examples, the machine-learning model 134 can be further enhanced through the use of a machine learning classifier, such as a recurrent neural network (RNN). This model can be trained using the calibration table described herein to predict various physiological properties as a function of signal characteristics, height, weight, age, and gender. This model can be useful when a particular set of signal and demographic information were not explicitly collected in the calibration table, and an algorithm is needed to make a prediction based on existing data.

Referring to FIG. 1B, in various examples, the mobile application 128 may further allow medical professionals 106 to input patient demographic information 130 for use by the controller 108. Demographic information 130 can be input into the mobile application 128 using either manual or automatic methods.

In various examples, manual input may require medical personnel 106 on site with the patient 104 to manually type, select, or write the demographic information 130 of the patient 104 into the mobile application 128 for use by the controller 108. Alternatively, medical personnel 106 may manually input such demographic information 130 by voice.

In various examples, medical personnel 106 may be able to automatically input demographic information 130. Automatic input may use computer vision technologies, which can be implemented with a camera and an app on a mobile computer device, with or without remote cloud computing, by photographing or scanning a patient 104, and then outputting an estimate for their demographic information 130, such as on the mobile application 128 of the mobile computing device 126 (whether computed by the mobile computing device 126 or received by the mobile computing device 126 from the cloud based on the image captured of the individual 104). Similarly, in various examples, computer vision technologies may be capable of scanning an identification card of the patient 104 which may have been found on or near the patient 104 to determine the demographic information 130 of the patient 104. In various examples, the controller 108 may be in wireless communication with a medical database, such that the medical personnel 106 can enter a patient identifier (e.g., the patient's name or phone number) to search the medical database and retrieve the medical data of the patient 104. Any of these options may be used to acquire the demographic information 130 of the patient 104, alone or in combination with one another.

Still referring to FIG. 1B, once the patient's demographic information 130 has been received by the controller 108, the controller 108 can select a machine-learning model 134 from a data store 132 comprising a collection of machine learning models (e.g., a model zoo) based on the demographic information 130 of the patient 104. In various examples, the data store 132 is comprised of a lookup table in which the patient's demographic information 130 can be used to select a model 134 that's learned demographic most closely matches the patient 104. In certain examples, the data store 132 can be comprised of a machine-learning classifier that uses the patient's demographic information 130 to classify the patient 104, and then selects a model from the model zoo that has a similar classification.

Referring again to FIG. 1B, the signals can be measured using the body-worn patch 102 and received by the controller 108. The controller 108 can then determine the physiological property of the patient 104 based on the selected machine-learning model 134 and the received signals.

Referring to FIGS. 1A-1B, once the physiological property has been determined by the controller 108, it can be displayed 180 by the mobile application 128 of the mobile computing device 126 or by another display.

Referring to FIG. 6A, the calculated physiological properties may be displayed 180 on the mobile computing device 126 via the mobile application 128. The physiological properties may be displayed in such a way that is familiar to medical personnel 106. In various examples, the display 180 may mirror current patient monitors by including the ECG signal 118, SCG signal 120, and/or PPG signal 122. Additionally, the display 180 may include the one or more physiological properties, such as heart rate, respiration rate, oxygen saturation, temperature, and/or blood pressure. Further, the color scheme of the mobile application 128 can be based on the color scheme of monitoring equipment that is currently in-use by medical professionals. By displaying vital signs and physiological properties in such a manner, the medical professionals can make quick judgements on the health of the patient, and make critical medical decisions based on this information.

Figure 1E:
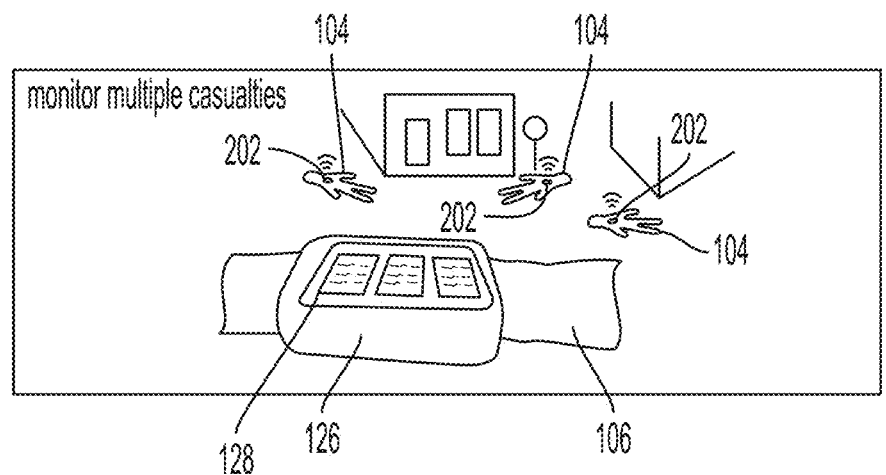
FIG. 1E illustrates simultaneously measuring physiological properties of multiple patients using body-worn patches in accordance with the present disclosure.
Figure 1F:
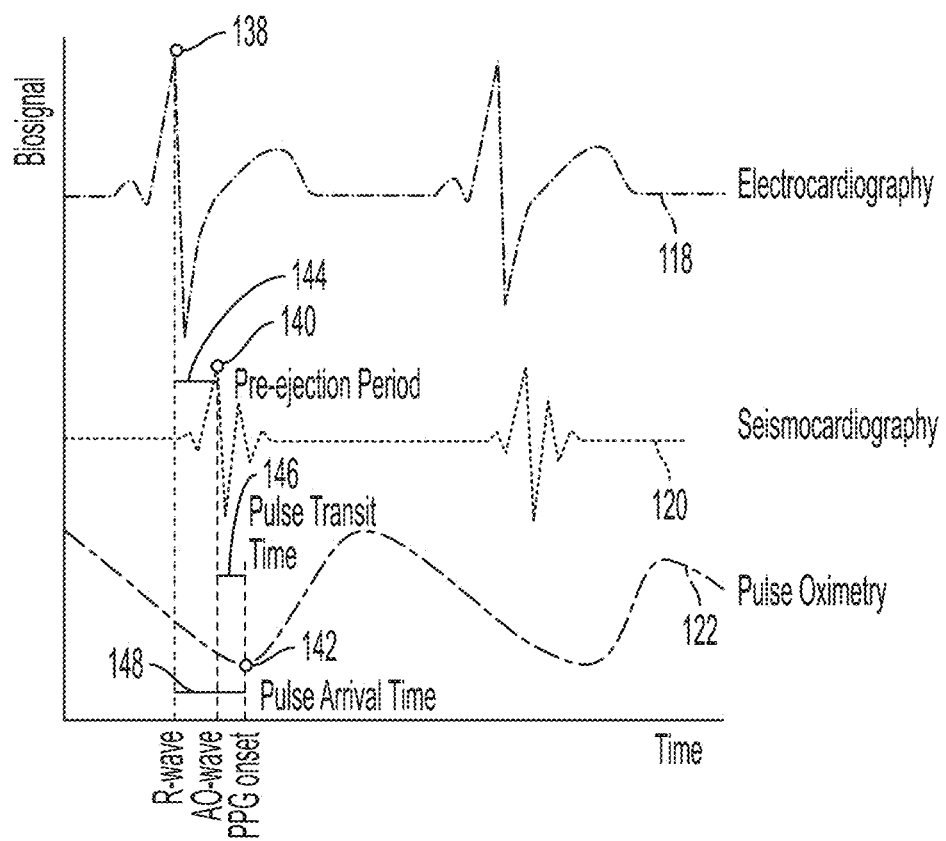
FIG. 1F illustrates a time-domain plot of multiple physiological signals measured by a body-worn patch in accordance with the present disclosure.

Referring to FIG. 1E, in various examples, the system may be capable of monitoring several patients 104 simultaneously. The mobile application 128 can pair with multiple body-worn patches 202 to simultaneously monitor the multiple patients 104 wearing the individual body-worn patches 202, which are all connected to the same mobile computing device 126. Each of the patients' vital signals and physiological properties can be visible to the healthcare professional 106 via the mobile computing device 126, such that they can monitor each of their patients 104 to determine which patient may need the most immediate assistance. Further, if any physiological properties of a patient drop below a certain threshold, indicating declining health conditions, the healthcare professional 106 can receive visible and auditory alarms to alert them to the patient 104 that is in need of attention.

Figure 7:
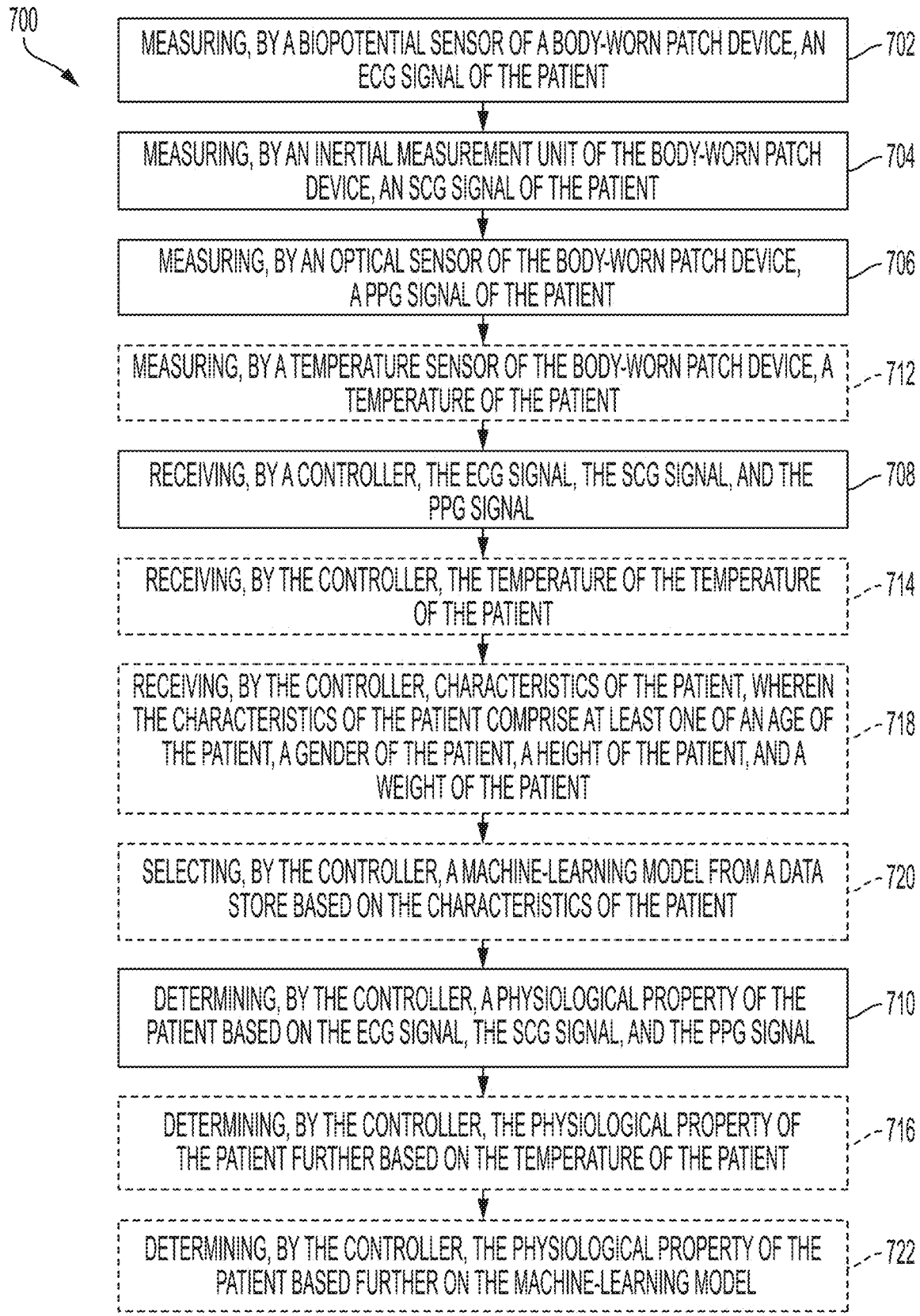
FIG. 7 is a method for determining a physiological property of a patient with a body-worn patch in accordance with the present disclosure.

Referring to FIG. 7, accordance with the present disclosure, a method 700 for determining a physiological property of a patient with a body-worn patch is disclosed. In various examples, prior to using the system, the body-worn patch may need to be turned on and the mobile application may need to be launched and connected to the body-worn patch. This may be done by a medical professional.

Referring to FIG. 1C, in various examples, the skin of the patient 104 may be prepped prior to applying the body-worn patch to the patient. As shown in FIG. 1C, skin preparation may include exposing the patient's skin, removing any body hair, abrading the area to remove dead skin and increase blood flow, wiping the area to clean, or any combination thereof. The body-worn patch may also be prepared by attaching the electrode to the housing by connecting any metallic electrode snaps and applying the device-side adhesive of the electrode to the housing of the body-worn patch. Once the electrode is attached to housing, the body-worn patch can be adhered to the patient by removing the skin-side adhesive liner and placing the body-worn patch on the skin that has been prepared.

Referring again to FIG. 7, the method for determining the physiological property of the patient with a body-worn patch can comprises measuring 702, by a biopotential sensor of a body-worn patch device, an ECG signal of the patient; measuring 704, by an inertial measurement unit of the body-worn patch device, an SCG signal of the patient; measuring 706, by an optical sensor of the body-worn patch device, a PPG signal of the patient; receiving 708, by a controller, the ECG signal, the SCG signal, and the PPG signal; and determining 710, by the controller, a physiological property of the patient based on the ECG signal, the SCG signal, and the PPG signal.

In further reference to FIG. 7, the method 700 can optionally further comprise measuring 712, by a temperature sensor of the body-worn patch device, a temperature of the patient; receiving 714, by the controller, the temperature of the patient; and determining 716, by the controller, the physiological property of the patient further based on the temperature of the patient.

In further reference to FIG. 7, the method can optionally further comprise receiving 718, by the controller, characteristics of the patient, wherein the characteristics of the patient comprise at least one of an age of the patient, a gender of the patient, a height of the patient, and a weight of the patient; selecting 720, by the controller, a machine learning model from a data store based on the characteristics of the patient; and determining 722, by the controller, the physiological property of the patient based further on the machine learning model.

EXAMPLE

One example of the system 100 described herein includes the ProPatch™ patch and the ProPatch™ Connect mobile application respectively, which together are referred to as the ProPatch™ Suite system. The ProPatch™ Suite system is a medical system that allows users to acquire detailed physiological information about an individual, including but not limited to vital signs such as heart rate (HR), respiration rate (Resp), oxygen saturation (SpO2), blood pressure (BP), and temperature (Temp), in a highly compact and portable form-factor. The ProPatch™ patch contains an array of sensors including a biopotential sensor, optical sensors, skin and environment temperature sensors, and an inertial measurement unit (IMU). The biopotential sensor can be configured to measure electrocardiogram (ECG), the optical sensors can perform photoplethysmography (PPG), and the IMU can measure seismocardiogram (SCG). ProPatch™ patch is affixed to the skin typically on the upper left chest via an electrode that functions dually to adhere the patch to the patient's chest and to create an electrically conductive pathway for biopotential measurements. Data is transmitted from the ProPatch™ patch to the ProPatch™ Connect mobile application via a wireless protocol such as Bluetooth®. A machine-learning algorithm uses data from the ProPatch™ patch to compute systolic and diastolic blood pressures. The ProPatch™ Connect mobile application displays the vital signs and bio signals in a fashion that is familiar to medical personnel, similar to current state-of-the-art patient monitors. Specifically, the display includes raw signals like electrocardiogram and photoplethysmography, and vital signs like heart rate, respiration rate, oxygen saturation, temperature, and blood pressure.

The exterior of ProPatch™ patch is comprised of a tough plastic enclosure, such as a polycarbonate/acrylonitrile butadiene styrene (PC/ABS). The plastic housing protects the electronics while pressing the sensors into the human skin to improve signal to noise ratio (SNR). Sensors such as the IMU and ECG sensors are secured on a printed circuit board (, and the printed circuit board is affixed to the plastic enclosure via screws. This ensures that the sensors themselves are not susceptible to movement within the plastic housing, which could affect the overall SNR of the system and measurements taken.

While most of the sensors are enclosed fully within the plastic housing, two of them, the PPG and temperature sensors, are visible from the outside. To mitigate potential breakage of the PPG sensor glass, protrusions are located around the perimeter of the patch bottom. These protrusions serve to protect the PPG sensor and are also referred to as the "Feet." The Feet are integrated into the plastic enclosure containing the skin-side sensors. Critically, the feet protrude further than the PPG sensor. For example, if the ProPatch™ patch were to be laid at rest on a flat table, with the skin-side sensors facing downwards to the table, then the feet would come into contact with the table while the PPG glass would remain floating and not touch the table. The temperature sensor is also a very delicate component and though it does not protrude as significantly from the case bottom as the PPG sensor it also has the potential to be damaged by external forces. A damaged temperature sensor will likely result in erroneous values being reported to medical professionals. Thus, the Feet which protrude from the case bottom serve to protect both of the protruding skin-side sensors of the ProPatch™ patch. When the device is placed on a soft surface such as a patient's skin, the skin deforms around the Feet, and the sensors are able to be pressed into the skin to generate measurements.

The disposable electrode that interfaces the ProPatch™ patch with the human body has multiple functions. First the electrode attaches to the ProPatch™ patch via a device-side adhesive and mechanical snaps, second it attaches to the patient's chest via a skin-side adhesive, and third it creates an electrically conductive pathway from the patient's chest to ProPatch™ patch for biopotential measurements (ex: ECG). A thick hydrogel constitutes the majority of the skin-side adhesive. The hydrogel is very tacky and adheres well to the human body even through dirt, sweat, and blood. An adhesive is present between the ProPatch™ patch and the electrode to increase the mechanical stability of the patch-electrode connection. Male electrode snaps are present on the electrode, which interface with the female electrode snaps on the ProPatch™ patch. The shape of the electrode itself is designed such that the electrode contacts a large surface area of the skin surrounding the conductive gel. The center area of the electrode is designed to interface with the ProPatch™ patch such that it does not hinder the functionality of the Feet or skin-side sensors. The electrode is designed to cover the USB port on the skin-side of the ProPatch™ patch such that the USB port is not accessible while in use, and does not make contact with the skin during use. For electrical safety and patient safety reasons, this physical barrier prevents the user from connecting a USB-cable to the ProPatch™ patch while it is in use on a patient.

Cutouts are present on the electrode around the male electrode snaps such that the electrode itself can deform out-of-plane to interface with the Wing shape of the ProPatch™ patch when the snaps are snapped into place. In some embodiments, this cutout is U-shaped. An identical cutout is present on the release liner of the Lifeware Labs' electrode. The U-shaped cutouts on both electrode and release liner also allow for the ProPatch™ patch to be snapped into the electrode before the electrode is removed from the release liner. In addition, cutouts can be made in the release liner to allow the Feet to protrude through the release liner. Healthcare professionals such as combat medics or EMT's have the option of attaching the electrode to Pro-Patch™ patch prior to their arrival on scene, such that the ProPatch™ patch need only be removed from the release liner and placed on a patient's chest. The release liner also houses an indentation for the sensing hydrogel, as it protrudes slightly from the electrode. The Wing shape of the ProPatch™ patch is designed such that the electrode snaps are physically further away from the patient's skin than the bottom sensors, and the U-shape cutouts on the electrode allow the male snaps to deform out-of-plane and meet the female snaps on the ProPatch™ patch. The majority of the skin-side adhesive is in contact with the patient's skin, while the U-shaped cutout allows the electrode snaps to deform away from the electrode such that it connects to the snaps of the ProPatch™ patch. The patch is pulled into the patient's chest via this combination of the Wing design and U-shaped cutouts surrounding the electrode snaps, forcing the skin to conform around the Feet, which in turn forces the skin-side sensors to be pressed into the skin for improved sensor SNR.

A patient receiving triage is typically transitioned into the supine position in order to assess their health state while stabilizing their body. The ProPatch™ patch is intended to be used during triage and thus applied to a patient after they are in the supine position. The supine position helps standardize the effects of hydrostatic pressure across a large population, and reduces the impact of incidental motion on sensor signal quality. For a good electrical connection and proper adhesion to the patient's skin, the ProPatch™ patch should not be worn over high concentrations of body hair. Body hair is non-conductive, and, when present, can increase the noise in a biopotential signal collection such as ECG, as well as interfere with optical measurements from the PPG sensor. Therefore, skin preparation should be performed at the application site, the upper left chest, prior to patch application. Skin preparation for the ProPatch™ patch starts by exposing the patient's chest and removing any body hair, such as with a disposable razor. Next, a rough pad is used to abrade the area to remove dead skin and increase blood flow to the surface due to hyperemia. An alcohol wipe is then used to clean any hair or debris. Once the area has been wiped clean by an alcohol wipe and any residual alcohol has dried or evaporated, the ProPatch™ patch can be adhered to the patient's chest. To attach the ProPatch™ patch to a patient, a disposable electrode is first attached to the ProPatch™ patch. The disposable electrode contains metal snaps and a double-sided adhesive that directly interfaces with ProPatch™ patch. Once the electrode is attached to ProPatch™ patch, the skin-side adhesive liner can be removed, and the ProPatch™ patch can be placed directly on the patient's chest and powered on to begin data collection and vitals monitoring. The ProPatch™ patch contains a multifunctional button on the environment side of the enclosure. In some embodiments, this button is made of an elastic material such as rubber, and is embossed with a common power icon.

The ProPatch™ patch is adhered to a patient's chest during triage and allows for the simultaneous collection of multiple raw signals such as electrocardiogram, seismocardiogram, and photoplethysmography. The ProPatch™ patch is designed to be used for triage by medical professionals, a situation where the patients being examined are most often in the supine position already, or will shortly be transferred to this position. Changes in the body's posture introduce differences in hydrostatic pressure in the circulatory system due to gravity. The supine position minimizes these effects on the subject's body and hence the supine position is recommended for blood pressure measurements with the ProPatch™ patch. The supine position also helps standardize the quality of the data across a broad population, therefore aiding with the general accuracy of the calculated vital signs. Finally, the supine position also helps reduce the effects of motion that can corrupt the raw sensor signals with unwanted noise, known as motion artifacts.

One non-limiting embodiment of the system architecture of the ProPatch™ Suite system is illustrated in FIG. 1A. A medical professional begins the use of the ProPatch™ patch by turning on the device, applying it on the patient, and subsequently launching the ProPatch™ Connect app and connecting to the ProPatch™ patch. In some embodiments, ProPatch™ patch samples the PPG and ECG raw signals at a rate of 200 Hz, while the Inertial Measurement Unit (IMU) is sampled at 100 Hz. The SCG data is acquired from the acceleration in the z-axis using the IMU, which aligns closely with the dorsoventral axis. Therefore, SCG is a measure of the dorsoventral accelerations of the chest wall due to the mechanical motion of the heart. The three raw signals acquired from the patient, ECG, SCG, and PPG, are used to derive various vital signs and intermediate metrics, also referred to as features. These features could relate to underlying physiological characteristics, and more specifically could relate to blood pressure characteristics. For example, these features could relate to the mechanical motion of the heart, the speed of the cardiovascular pulse pressure wave, or the shape of the cardiovascular pulse pressure wave. The raw signals, vital signs, and features are used in a machine-learning model to calculate blood pressure. In some embodiments, classical machine learning models like linear regression, decision trees and its variants, gradient boosted machines or ensemble methods, are used, while in other embodiments deep learning based neural network models are used. The intermediate metrics can be computed on either the ProPatch™ patch or on the ProPatch™ Connect mobile application. In some embodiments, the derived intermediate metrics are computed locally on the ProPatch™ patch and are transmitted to the ProPatch™ Connect app via Bluetooth®, where the machine-learning model makes blood pressure prediction. Predicted systolic and diastolic pressure values are displayed on the ProPatch™ Connect application, along with other vitals computed onboard the ProPatch™ patch, for the medical professional to interpret.

The predicted BP values, which are based on the ProPatch™ patch data and features derived from ECG, PPG, and SCG, can provide an indication of a patient's health state and allows the triaging medical professional to have a near-immediate understanding of the treatment necessary. The inclusion of patient demographics can further enhance the BP predictions created by the ProPatch™ Suite system, since demographics help to account for anatomical differences between patients. In some embodiments, the mobile application allows the medical professional to input demographics. Demographics can be inputted into the ProPatch™ Connect mobile application using either manual or automatic methods. Manual input of demographics may be done by hand or by voice. Automatic input of demographics may be done by visual means. For example, the camera of the mobile device that is running the ProPatch™ Connect mobile application can capture images of the patient, and a machine learning classifier can use these images to estimate the patient's demographics, as described in U.S. patent application Ser. No. 17/474,906. Another automatic input method may be through inputting the patient's name and retrieving their demographics from a cloud repository such as an electronic health record. A third automatic method could use the mobile device's camera to scan the patient's driver's license, or other identification card, to acquire their demographics. Demographics can be used for blood pressure predictions or the calculation of other vitals by providing a priori information that can help refine existing predictions or make new predictions that take the demographic factors into account. These demographic factors include height, weight, body mass index (BMI), sex, and age. Patient demographics also play a large role in cardiac fitness, cardiovascular arterial wall and venous wall stiffnesses, anatomical geometries including geometries of the cardiovascular system, and other genetic-related factors. Hence, differences in demographics can have an effect on training blood pressure models, and thus deployed blood pressure models.

The accuracy of BP predictions can be enhanced through the use of patient demographics and a model zoo, FIG. 1B, where a model zoo is a collection of machine learning models. For example, the ProPatch™ Connect mobile application can use patient demographics to make enhanced BP predictions using a model zoo that is comprised of an array of BP machine learning models each trained on specific sub-populations representing a variety of demographic groupings. A model selection module selects an ensemble of BP models from the model zoo based on patient demographics and custom metrics. In some embodiments, the model selection module is comprised of a lookup table in which the patient's demographics, such as age, weight, height, and sex, are used to select a model that's learned demographic most closely matches the patient. In other embodiments, the model selection module is comprised of a machine learning classifier that uses the patient's demographics to classify the patient, and then selects a model from the model zoo that has a similar classification. The mobile application can use the selected model ensemble for the entirety of the triage situation. The model ensemble uses the patient's demographic information and the data received from the ProPatch™ patch to produce enhanced blood pressure predictions. An enhanced blood pressure value that is closest to the true blood pressure value will be the most valuable to a medical professional in determining the health state of a patient during a triage situation. The enhanced BP predictions are then used to update the displayed BP.

The ProPatch™ Connect mobile application is paired to the ProPatch™ patch via a wireless connection such as Bluetooth®. Over this connection, raw signals such as ECG, PPG, and SCG waveforms are received and displayed to the medical professional. The processing unit, located within the electronics of the ProPatch™ patch, calculates a variety of vital signs, intermediate metrics for BP prediction, and remaining battery percent. These values, in addition to software version numbers and other statistics, are transmitted to the ProPatch™ Connect mobile application. The vitals and battery information are displayed in real-time on the mobile device screen as in FIG. 6A. Intermediate metrics, such as those needed for BP prediction, are received by the mobile application, run through an integrated machine learning algorithm to make a BP prediction, and the predicted BP is displayed as systole over diastole on the screen. For a multi-casualty situation, ProPatch™ Connect has the ability to display the vitals of multiple patients on one screen, allowing the healthcare professional to care for and prioritize multiple wounded. ECG and PPG waveforms are displayed to the medical professional in real-time, allowing them the ability to detect abnormalities in these raw signals, due to the speed at which the signals are displayed. Abnormalities in raw waveforms could indicate that immediate treatment is required, such as tachycardia or bradycardia. The ProPatch™ Connect application was designed in a landscape fashion, although portrait orientation is available. The ProPatch™ Connect mobile application also has a variety of audio and visual alarms, such as a heart rate audio indicator and SpO2 audio indicator to directly alert the medical professional to a patient's vitals.

The ProPatch™ Suite system is capable of monitoring several patients simultaneously. The ProPatch™ Connect application can pair to multiple ProPatch™ patches simultaneously to monitor the vitals of multiple wounded individuals from a single device running a ProPatch™ Connect application. For example, this system is ideal for a mass casualty situation where there are multiple wounded, and in many cases, more patients than there are healthcare professionals. A healthcare professional can assess a patient, perform skin preparation, and apply a ProPatch™ patch to their upper left chest. The medical personnel can then assess the patient's health and determine whether or not immediate treatment is necessary. In cases where wounds are minor or treatment is not determined to be immediately necessary, the healthcare professional can move on to other patients, applying a new ProPatch™ patch for each patient. All of the patients' vitals will be visible to the healthcare professional, and they can monitor each of their patients to determine which are in the most immediate need of assistance. When vitals drop below a certain threshold, indicating declining health conditions, the healthcare professional will receive visible and auditory alarms to alert them to the patient that is in dire need of attention.

The ProPatch™ Suite system is capable of transmitting vital signs from the ProPatch™ Connect app over the internet, or other wireless communication protocol, to a remote medical personnel. For example, a patient who is being monitored via the ProPatch™ Suite system can have their vital signs and other physiological data streamed to a remote medical personnel who can then guide the onsite medical personnel with specific care instructions. Or, the remote medical personnel could be a hospital staff member preparing to receive the patient who is being monitored by the ProPatch™ Suite system. In some embodiments, the remote medical personnel is an artificial intelligence software that is trained to triage and identify possible pathologies, and then instruct the onsite medical personnel with specific care.

Those skilled in the art will recognize that the herein described compositions, articles, methods, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific exemplar is intended to be representative of its class, and the non-inclusion of specific components (e.g., operations), devices, and objects should not be taken as limiting.

With respect to the appended claims, those skilled in the art will appreciate that recited operations therein may generally be performed in any order. Also, although various operational flows are presented in a sequence(s), it should be understood that the various operations may be performed in other orders than those that are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various examples have been described herein, many modifications, variations, substitutions, changes, and equivalents to those examples may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed examples. The following claims are intended to cover all such modification and variations.

Various aspects of the disclosure according to the present disclosure include, but are not limited to, the aspects listed in the following numbered clauses.

Clause 1. A system comprising: a body-worn patch to be worn by a patient, wherein the body-worn patch comprises a plurality of sensors, wherein the plurality of sensors comprises: a biopotential sensor capable of measuring an electrocardiogram (ECG) signal, an inertial measurement unit capable of measuring a seismocardiogram (SCG) signal, an optical sensor capable of measuring a photoplethysmography (PPG) signal; and a controller in signal communication with the plurality of sensors and the controller is capable of receiving the ECG signal, the SCG signal, and the PPG signal, wherein the controller is capable of determining a physiological property of the patient based on the ECG signal, the SCG signal, and the PPG signal.

Clause 2. The system of clause 1, wherein the controller is capable of aligning the ECG signal, the SCG signal, and the PPG signal based on time, and wherein the controller is capable of determining the physiological property of the patient based on a plurality of characteristics from the aligned ECG signal, SCG signal, and PPG signal.

Clause 3. The system of any of clause 1-2, wherein the plurality of characteristics comprises a pre-ejection period based on an R-wave of the ECG signal and an AO peak of the SCG signal.

Clause 4. The system of any of clauses 1-3, wherein the plurality of characteristics comprises a pulse transit time based on an AO peak of the SCG signal and a PPG onset of the PPG signal.

Clause 5. The system of any of clauses 1-4, wherein the plurality of characteristics comprises a pulse arrival time based on an R-wave of the ECG signal and a PPG onset of the PPG signal.

Clause 6. The system of any of clauses 1-5, wherein the plurality of characteristics comprise: a pre-ejection period based on an R-wave of the ECG signal and an AO peak of the SCG signal; a pulse transit time based on the AO peak of the SCG signal and a PPG onset of the PPG signal; and a pulse arrival time based on the R-wave of the ECG signal and the PPG onset of the PPG signal.

Clause 7. The system of any of clauses 1-6, wherein the controller is capable of determining the physiological property of the patient using a machine-learning model.

Clause 8. The system of clause 7, wherein the machine-learning model comprises at least one model selected from the group consisting of: linear regression, decision tree, gradient boosted machine, ensemble method, and a deep learning based neural network.

Clause 9. The system of any of clauses 1-8, wherein the biopotential sensor comprises at least two electrodes removably connected to the body-worn patch, wherein the electrodes contact a skin of the patient to make an electrical connection between the patient and the body-worn patch.

Clause 10. The system of any of clauses 1-9, wherein the plurality of sensors further comprises a temperature sensor.

Clause 11. The system of clause 10, wherein at least one of the optical sensor and the temperature sensor contacts a skin of the patient.

Clause 12. The system of any of clauses 1-11, wherein the body-worn patch further comprises a wireless communication circuit capable of wirelessly transmitting the ECG signal, the SCG signal, and the PPG signal to the controller, a secondary controller, or a combination thereof.

Clause 13. The system of clause 12, wherein the wireless communication circuit transmits the ECG signal, the SCG signal, and the PPG signal using Bluetooth.

Clause 14. The system of any of clauses 1-13, wherein the controller is further capable of receiving characteristics of the patient, wherein the controller determines the physiological property based on the ECG signal, the SCG signal, the PPG signal, and the characteristics of the patient.

Clause 15. The system of clause 14, wherein the characteristics of the patient comprise at least one of an age of the patient, a gender of the patient, a height of the patient, and a weight of the patient.

Clause 16. The system of clause 15, wherein the characteristics of the patient are determined based on a manual input by a user to the controller, a first scan of an identification card of the patient, a second scan of the patient by a camera connected to the controller, an automatic retrieval from a medical database wherein the medical database comprises medical data of the patient, or a combination thereof.

Clause 17. The system of any of clauses 14-16, wherein the controller selects a machine learning model from a data store based on the characteristics of the patient and the controller determine the physiological property of the patient based on the machine learning model.

Clause 18. A method for determining a physiological property of a patient with a body-worn patch, the method comprising: measuring, by a biopotential sensor of a body-worn patch device, an ECG signal of the patient; measuring, by an inertial measurement unit of the body-worn patch device, an SCG signal of the patient; measuring, by an optical sensor of the body-worn patch device, a PPG signal of the patient; receiving, by a controller, the ECG signal, the SCG signal, and the PPG signal; and determining, by the controller, a physiological property of the patient based on the ECG signal, the SCG signal, and the PPG signal.

Clause 19. The method of clause 18, herein the method further comprises: measuring, by a temperature sensor of the body-worn patch device, a temperature of the patient; receiving, by the controller, the temperature of the temperature of the patient; and determining, by the controller, the physiological property of the patient further based on the temperature of the patient.

Clause 20. The method of any of clauses 18-19, wherein the method further comprises: receiving, by the controller, characteristics of the patient, wherein the characteristics of the patient comprise at least one of an age of the patient, a gender of the patient, a height of the patient, and a weight of the patient; selecting, by the controller, a machine learning model from a data store based on the characteristics of the patient; and determining, by the controller, the physiological property of the patient based further on the machine learning model.

As used herein, "at least one of" a list of elements means one of the elements or any combination of two or more of the listed elements. As an example "at least of A, B, and C" means A only; B only; C only; A and B; A and C; B and C; or A, B, and C.

Various features and characteristics are described in this specification to provide an understanding of the apparatus, structure, production, function, and/or operation of the present disclosure, which includes the disclosed apparatus and methods. It is understood that the various features and characteristics of the present disclosure described in this specification can be combined in any suitable manner, regardless of whether such features and characteristics are expressly described in combination in this specification. The Inventors and the Applicant expressly intend such combinations of features and characteristics to be included within the scope of the present disclosure described in this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims and will comply with the written description, sufficiency of description, and added matter requirements. The various non-limiting embodiments disclosed and described in this specification can comprise, consist of, or consist essentially of the features and characteristics as variously described herein.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with the written description, sufficiency of description, and added matter requirements.

Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameters.

Notwithstanding that numerical ranges and parameters setting forth the broad scope of the present disclosure are approximations, numerical values set forth in the specific examples are reported precisely as possible. Any numerical value, however, inherently contains certain errors necessarily resulting from the standard variation found in its respective testing measurements.

Reference throughout the specification to "various examples," "some examples," "one example," "an example," or the like means that a particular feature, structure, or characteristic described in connection with the example is included in an example. Thus, appearances of the phrases "in various examples," "in some examples," "in one example," "in an example," or the like, in places throughout the specification are not necessarily all referring to the same example. Furthermore, the particular features, structures, or characteristics may be combined in any suitable manner in an example or examples. Thus, the particular features, structures, or characteristics illustrated or described in connection with one example may be combined, in whole or in part, with the features, structures, or characteristics of another example or other examples without limitation. Such modifications and variations are intended to be included within the scope of the present examples.

Any patent, publication, or other document identified in this specification is incorporated by reference into this specification in its entirety unless otherwise indicated but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with the written description, sufficiency of description, and added matter requirements.

Whereas particular examples of this present disclosure have been described above for purposes of illustration, it will be evident to those skilled in the art that numerous variations of the details of the present disclosure may be made without departing from the present disclosure as defined in the appended claims.

While the present disclosure provides descriptions of various specific aspects for the purpose of illustrating various aspects of the present disclosure and/or its potential applications, it is understood that variations and modifications will occur to those skilled in the art. Accordingly, the present disclosure should be understood to be at least as broad as they are claimed and not as more narrowly defined by particular illustrative aspects provided herein.

It is understood that this specification is not limited to the examples summarized in the Summary or Detailed Description. Various other aspects are described and exemplified herein.

What is claimed is:

1. A system comprising:
a body-worn patch to be worn by a subject, wherein the body-worn patch comprises
a housing comprising a first surface and a second surface;

an optical sensor capable of measuring a photoplethysmography (PPG) signal and the optical sensor protruding from the first surface of the housing a first distance; and
protrusions positioned about the first surface, wherein the protrusions extend from the first surface of the housing a second distance, the second distance is greater than the first distance;
wherein there are at least four protrusions;
wherein the protrusions are capable to protect the optical sensor from physical damage while enabling a soft surface to deform around the protrusions and contact the optical sensor; and
a controller in signal communication with the optical sensor and the controller is capable of receiving the PPG signal, wherein the controller is capable of determining a physiological property of the subject based on the PPG signal.

2. The system of claim 1, wherein the protrusions are integrated into the housing.

3. The system of claim 1, wherein the protrusions are rounded.

4. The system of claim 1, wherein the first distance is in a range of 0.05 mm to 5 mm.

5. The system of claim 1, wherein the first distance is in a range of 0.5 mm to 2.5 mm.

6. The system of claim 1, further comprising at least two electrodes removably connected to the body-worn patch, wherein the electrodes are configured to contact a skin of the subject to make an electrical connection between the subject and the body-worn patch.

7. The system of claim 6, wherein the body-worn patch is located between the at least two electrodes.

8. The system of claim 7, wherein the at least two electrodes are connected to the body-worn patch by fasteners.

9. The system of claim 8, wherein the fasteners are positioned away from the first surface of the housing.

10. The system of claim 8, wherein the fasteners are mechanical snaps.

11. The system of claim 10, wherein the housing comprises curved corners to position the fasteners away from skin of the subject.

12. The system of claim 7, wherein the at least two electrodes comprise an adhesive capable of attaching to skin of the subject.

13. The system of claim 12, wherein the at least two electrodes define a first plane such that when the at least two electrodes are attached to the skin of the subject, the at least two electrodes are configured to pull the body-worn patch down into the skin of the subject.

14. The system of claim 1, wherein the body-worn patch is wing shaped.

15. The system of claim 1, wherein the body-worn patch further comprises a temperature sensor protruding from the first surface a third distance, wherein the third distance is less than the second distance.

16. The system of claim 1, wherein the protrusions are positioned about a perimeter of the first surface.

17. A method for determining the physiological property of the subject with the body-worn patch of claim 1, the method comprising:
applying the body-worn patch to skin of the subject such that the optical sensor and the protrusions contact the skin of the subject;
measuring, by the optical sensor of the body-worn patch, the PPG signal of the subject;
receiving, by the controller, the PPG signal; and
determining, by the controller, the physiological property of the subject based on the PPG signal.

18. The method of claim 17, wherein the method further comprises:
measuring, by a temperature sensor of the body-worn patch, a temperature of the subject;
receiving, by the controller, the temperature of the subject; and
determining, by the controller, the physiological property of the subject further based on the temperature of the subject.

19. The system of claim 1, wherein the first surface is substantially planar.

20. The system of claim 1, wherein the first surface is an exterior surface.

21. The system of claim 1, wherein the first surface extends furthest from the second surface compared to a remainder of the housing except for the protrusions.

22. The system of claim 1, wherein sides of the protrusions are exposed.

23. A system comprising:
a body-worn patch to be worn by a subject, wherein the body-worn patch comprises a housing comprising a first surface and a second surface;
an optical sensor capable of measuring a photoplethysmography (PPG) signal and the optical sensor protruding from the first surface of the housing a first distance; and
protrusions positioned about the first surface, wherein the protrusions extend from the first surface of the housing a second distance, the second distance is greater than the first distance;
wherein there are at least four protrusions;
wherein each protrusion includes a distal end, and each distal end is separated from each other by at least a gap; and
a controller in signal communication with the optical sensor and the controller is capable of receiving the PPG signal, wherein the controller is capable of determining a physiological property of the subject based on the PPG signal;
wherein the protrusions are capable to protect the optical sensor from physical damage while enabling a soft surface to deform around the protrusions and contact the optical sensor.

24. A system comprising:
a body-worn patch to be worn by a subject, wherein the body-worn patch comprises a housing comprising a first surface and a second surface;
an optical sensor capable of measuring a photoplethysmography (PPG) signal and the optical sensor protruding from the first surface of the housing a first distance; and
protrusions positioned about the first surface, wherein the protrusions extend from the first surface of the housing a second distance, the second distance is greater than the first distance;
wherein the first surface is substantially planar; and
a controller in signal communication with the optical sensor and the controller is capable of receiving the PPG signal, wherein the controller is capable of determining a physiological property of the subject based on the PPG signal;
wherein the protrusions are capable to protect the optical sensor from physical damage while enabling a soft surface to deform around the protrusions and contact the optical sensor.

* * * * *